US012582406B2

(12) United States Patent
Okada

(10) Patent No.: US 12,582,406 B2
(45) Date of Patent: Mar. 24, 2026

(54) CARTRIDGE AND CARTRIDGE SYSTEM

(71) Applicant: OLYMPUS MEDICAL SYSTEMS CORP., Tokyo (JP)

(72) Inventor: Tsutomu Okada, Tachikawa (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 123 days.

(21) Appl. No.: 18/427,178

(22) Filed: Jan. 30, 2024

(65) Prior Publication Data

US 2024/0260969 A1      Aug. 8, 2024

Related U.S. Application Data

(60) Provisional application No. 63/483,084, filed on Feb. 3, 2023.

(51) Int. Cl.
*A61B 17/122* (2006.01)
*A61B 17/00* (2006.01)

(52) U.S. Cl.
CPC .... *A61B 17/1222* (2013.01); *A61B 17/00234* (2013.01); *A61B 2017/00982* (2013.01)

(58) Field of Classification Search
CPC .......... A61B 17/1222; A61B 17/00234; A61B 2017/00982; A61B 17/1227; A61B 2017/00902; A61B 17/1285; A61B 2017/0053; A61B 17/122; A61B 17/128; A61B 17/12; A61B 17/105; A61B 17/072; A61B 17/068; A61B 2017/00398; A61B 17/07207; A61B 2017/07214; A61B 2017/07271; A61B 17/083; A61B 17/10
See application file for complete search history.

(56) References Cited

U.S. PATENT DOCUMENTS

2007/0112359 A1      5/2007   Kimura et al.
2022/0401106 A1    12/2022   Okada
2024/0260968 A1      8/2024   Okada

FOREIGN PATENT DOCUMENTS

WO      WO-2021171407 A1      9/2021

OTHER PUBLICATIONS

U.S. Appl. No. 18/427,101, Non Final Office Action mailed Jul. 30, 2025, 16 pgs.
U.S. Appl. No. 18/427,101, Response filed Oct. 30, 2025 to Non Final Office Action mailed Jul. 30, 2025, 11 pgs.

*Primary Examiner* — Tan-Uyen T Ho
*Assistant Examiner* — Bridget E. Rabaglia
(74) *Attorney, Agent, or Firm* — Schwegman Lundberg & Woessner, P.A.

(57) ABSTRACT

A cartridge configured to store a clip unit is disclosed herein. The first cartridge includes a sheath connection portion configured to receive a sheath of an applicator. The second cartridge included a storage area configured to store at least a part of the clip unit. The second cartridge is movable relative to the first cartridge in a moving direction of the clip unit.

20 Claims, 30 Drawing Sheets

CARTRIDGE AND CARTRIDGE SYSTEM

CROSS-REFERENCE TO RELATED APPLICATIONS

The present application claims priority based on U.S. Patent Provisional Application No. 63/483,084 provisionally filed in the United States on Feb. 3, 2023, the contents of which are incorporated herein by reference.

TECHNICAL FIELD

The present disclosure relates to a cartridge and a cartridge system.

BACKGROUND

In endoscopic therapy, a clip unit that can ligate an excised part or the like after treatment to stop bleeding or the like may be used. The clip unit may include a clip that nips an excised part or the like and a presser tube that accommodates the clip and locks the clip in a closed state. The clip unit can be introduced into a treatment position by an applicator (an introduction device) which can be inserted into a channel of an endoscope.

PCT International Publication No. WO 2021/171407 (Patent Document 1) discusses a cartridge system that can reload a clip unit into an applicator. A user can load a clip unit to an applicator using the cartridge system.

SUMMARY

In the cartridge disclosed in Patent Document 1, when a clip unit is loaded to an applicator using the cartridge system, it is necessary to properly insert the applicator into the cartridge such that a gap is not formed between the clip unit and the applicator.

In consideration of the aforementioned circumstances, the present disclosure is directed to a cartridge and a cartridge system that can make it difficult to form a gap between a clip unit and an applicator and more reliably load the clip unit into the applicator.

A cartridge according to a first aspect of the present disclosure may store a clip unit. The cartridge includes a first cartridge and a second cartridge. The first cartridge includes a sheath connection portion configured to receive a sheath of an applicator. The second cartridge included a storage area configured to store at least a part of the clip unit. The second cartridge is movable relative to the first cartridge in a moving direction of the clip unit.

With the cartridge and the cartridge system according to the present disclosure, it is possible to make it difficult to form a gap between a clip unit and an applicator and to more reliably load the clip unit into the applicator.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 5 is a sectional view of the cartridge in which the clip unit is stored.

FIG. 22 is a diagram illustrating the clip unit which is introduced into a body using the clip introduction device.

DETAILED DESCRIPTION OF THE INVENTION

First Embodiment

Figure 1:
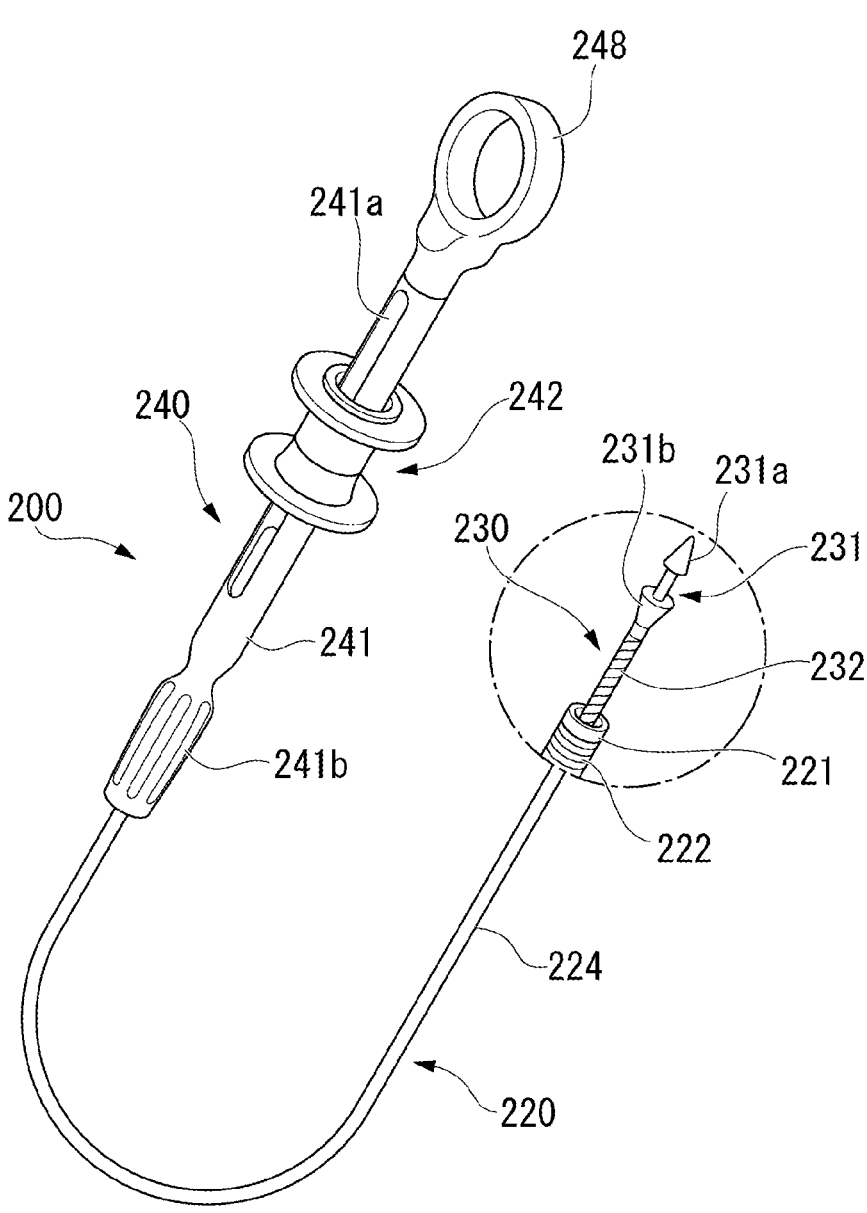
FIG. 1 is a perspective view of a clip introduction device.

A first embodiment of the present disclosure will be described below with reference to FIGS. 1 to 26.

A cartridge system 100 according to this embodiment may include a clip unit 1 and a cartridge 5 that accommodates, locates, or stores the clip unit 1. The cartridge system 100 may function or operate as a support system that allows the clip unit 1 to be easily loaded into a clip introduction device 200. The clip introduction device 200 and the clip unit 1 loaded into the clip introduction device 200 are also referred to as a clip device 300 (see FIG. 22).

Clip Introduction Device 200

FIG. 1 is a perspective view of the clip introduction device 200.

The clip introduction device (applicator) 200 may include a sheath 220, an operating wire 230, and an operation portion 240. The clip introduction device 200 may be inserted into, for example, a treatment tool insertion channel of an endoscope and may be used in combination with the endoscope. Accordingly, the sheath 220 may be formed to be much longer than a length of the treatment tool insertion channel of the endoscope. The sheath 220 may be at least partially flexible and may be curved according to a curvature of an insertion portion of the endoscope.

The sheath 220 may include a distal tip 221, a distal-side coil 222, and a proximal-side coil 224 and may be formed in a long and thin tubular shape as a whole. The distal-side coil 222 may be disposed on the tip side of the sheath 220. The distal tip 221 may be disposed at the tip of the distal-side coil 222.

As illustrated in FIG. 1, the operating wire (power transmission portion) 230 may include an arrowhead-shaped hook portion (connection portion) 231 connected to the clip unit 1 and a wire 232 that may be used to operate the arrowhead-shaped hook portion 231.

The arrowhead-shaped hook portion 231 may include an engagement portion 231*a* with a substantially conic shape engaging with the clip unit 1 and a wire connection portion 231*b* that is provided at a base end of the engagement portion 231*a*. The arrowhead-shaped hook portion 231 may be formed of, for example, a metallic material such as a stainless steel material.

The wire 232 may be movably inserted into the sheath 220. A tip of the wire 232 may be fixed to a base end of the wire connection portion 231*b*, for example, by welding.

As illustrated in FIG. 1, the operation portion 240 may include an operation portion body 241, a slider 242, and a thumb ring 248. The operation portion body 241, the slider 242, and the thumb ring 248 may be formed, for example, by injection-molding a resin material. The operation portion body 241 may include a slit portion 241*a* and a rotary grip 241*b* on a tip side thereof. The slit portion 241*a* may support the slider 242 such that the slider 242 may be movable.

The slider 242 may be attached to be movable in a longitudinal axis direction of the operation portion body 241, and a base end of the wire 232 may be attached thereto. When the slider 242 moves forward and backward along the operation portion body 241, the wire 232 moves forward and backward relative to the sheath 220, and thus the arrowhead-shaped hook portion 231 moves forward and backward.

The thumb ring 248 may be attached to the base end of the operation portion body 241 such that the thumb ring 248 may be rotatable around the longitudinal axis of the operation portion body 241.

Clip Unit 1

Figure 2:
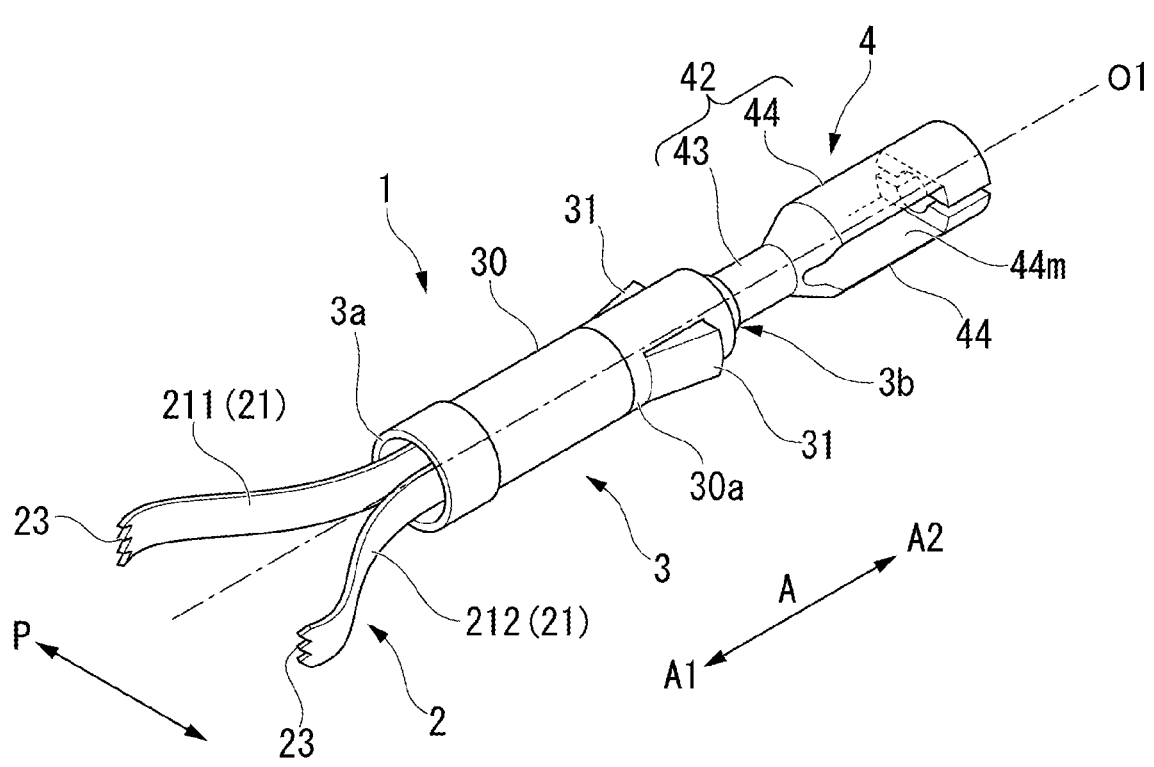
FIG. 2 is a perspective view of a clip unit of a cartridge system according to a first embodiment.
Figure 3:
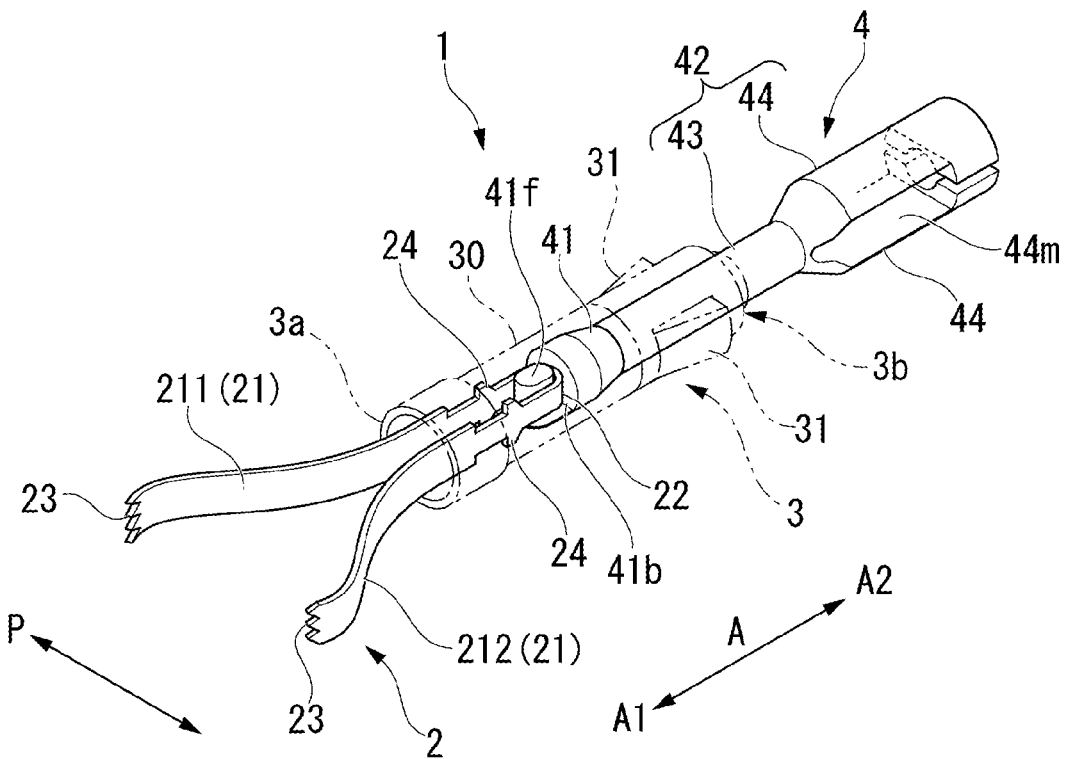
FIG. 3 is a perspective view of the clip unit transparently illustrating a presser tube.

FIG. 2 is a perspective view of the clip unit 1 of the cartridge system 100 according to this embodiment. FIG. 3 is a perspective view of the clip unit 1 transparently illustrating the presser tube 3. The clip unit 1 may include a clip 2, a presser tube (pipe) 3 serving as a fixing member, and a connection member (connector) 4. In the following description, the clip 2 side in a length direction A of the clip unit 1 may be defined as a tip side (a distal side) A1 of the clip unit, and the connection member 4 side may be defined as a base side (a proximal side) A2 of the clip unit 1.

The clip 2 may be formed, for example, by bending a metallic plate member such as a leaf spring member formed of a stainless steel material at a central portion thereof. The clip 2 may include a pair of arms 21 that can be opened and closed and a connection portion 22 that connects the pair of arms 21.

The pair of arms 21 includes a first arm 211 and a second arm 212. The first arm 211 and the second arm 212 may be disposed symmetric with respect to a center axis O1 in the length direction A of the clip unit 1. Tissue grasping portions 23 facing each other may be formed at the tips of the pair of arms 21. The tissue grasping portions 23 may be formed such that the tips of the pair of arms 21 are bent inward.

An engagement portion 24 protruding in a direction perpendicular to the center axis O1 may be formed at the base end of the pair of arms 21. The tissue grasping portion 23 side of the engagement portion 24 may be formed as a slope with an acute angle, and the connection portion 22 side of the engagement portion 24 may be formed as a slope with an obtuse angle.

The connection portion 22 may be bent and formed in a U-shape and may be connected to the connection member 4. The connection portion 22 may be biased such that the pair of arms 21 are in an open state. Accordingly, the pair of arms 21 of the clip 2 may have a self-expanding force in an opening or closing direction P.

The presser tube 3 may include a presser tube body 30 formed in a tubular shape and a protruding or retracting wing 31. The presser tube body 30 may be formed by injection-molding a resin material with high rigidity. The presser tube body 30 may be formed of metal instead of a resin material with high rigidity. The protruding or retracting wing 31 may be formed by injection molding a material softer than the clip 2, for example, a resin material with high rigidity and with appropriate elasticity such as polyphthalamide (PPA) or polyamide (PA).

The protruding or retracting wing 31 may be a pair of protrusions that protrudes and retracts with respect to an outer circumferential surface 30a of the presser tube body 30. The protruding or retracting wing 31 may be provided on both sides with the center axis O1 interposed therebetween. The protruding or retracting wing 31 may have a protruded state in which the protruding or retracting wing 31 protrudes outward in a radial direction from the outer circumferential surface 30a as a basic posture. The protruding or retracting wing 31 may be switched to a retracted state in which the protruding or retracting wing 31 retracts from the outer circumferential surface 30a with a force acting from the outside to the inside in the radial direction. By releasing the force, the protruding or retracting wing 31 may be returned from the retracted state to the protruded state.

The connection member 4 may be connected to the connection portion 22 of the clip 2. The connection member 4 may be connected to the arrowhead-shaped hook portion 231 inserted into the sheath 220. That is, the connection member 4 may connect the clip 2 and the arrowhead-shaped hook portion 231. The connection member 4 may 4 may include an insertion portion 41 that may be inserted into an internal space of the presser tube 3 and a connection portion 42 that may be provided at a base end of the insertion portion 41.

The insertion portion 41 may be an engagement portion that engages with (e.g., is connected to) the connection portion 22 of the clip 2. The insertion portion 41 may include a hook 41f that is provided on the tip side A1 and a breakable portion 41b that is provided on the base side A2 of the hook 41f. The hook 41f may be a hook extending in a direction perpendicular to the center axis O1 and may be formed in a substantially cylindrical rod shape. The connection portion 22 of the clip 2 may be hooked to the hook 41f.

The breakable portion 41b may be broken when a breaking force based on pulling of, for example, 20 N to 90 N is applied to the hook 41f because the connection portion 22 is pulled to the base side A2. The breakable portion 41b may include a mechanism for disconnecting the connection portion 22 of the clip 2 and the hook 41f of the connection member 4. For example, the breakable portion 41b may be a mechanism for disconnecting the connection portion 22 and the hook 41f through deformation without being broken (plastic deformation or elastic deformation).

The connection portion 42 may be an engagement portion that engages with (e.g., is connected to) the arrowhead-shaped hook portion 231 of the clip introduction device 200.

The connection portion 42 may include a connection portion body 43 and an elastic arm portion 44.

The elastic arm portion 44 may be provided at a base end of the connection portion body 43 and branches in a bifurcated shape. The elastic arm portion 44 can be elastically deformed relative to the connection portion body 43 and can be opened and closed with respect to the connection portion body 43. A cutout portion 44m that grasps and accommodates, locates, or stores the engagement portion 231a of the arrowhead-shaped hook portion 231 may be formed in the elastic arm portion 44. The cutout portion 44m may be formed in a shape which is in close contact with the outer circumferential surface of the engagement portion 231a of the arrowhead-shaped hook portion 231.

Cartridge 5

Figure 4:
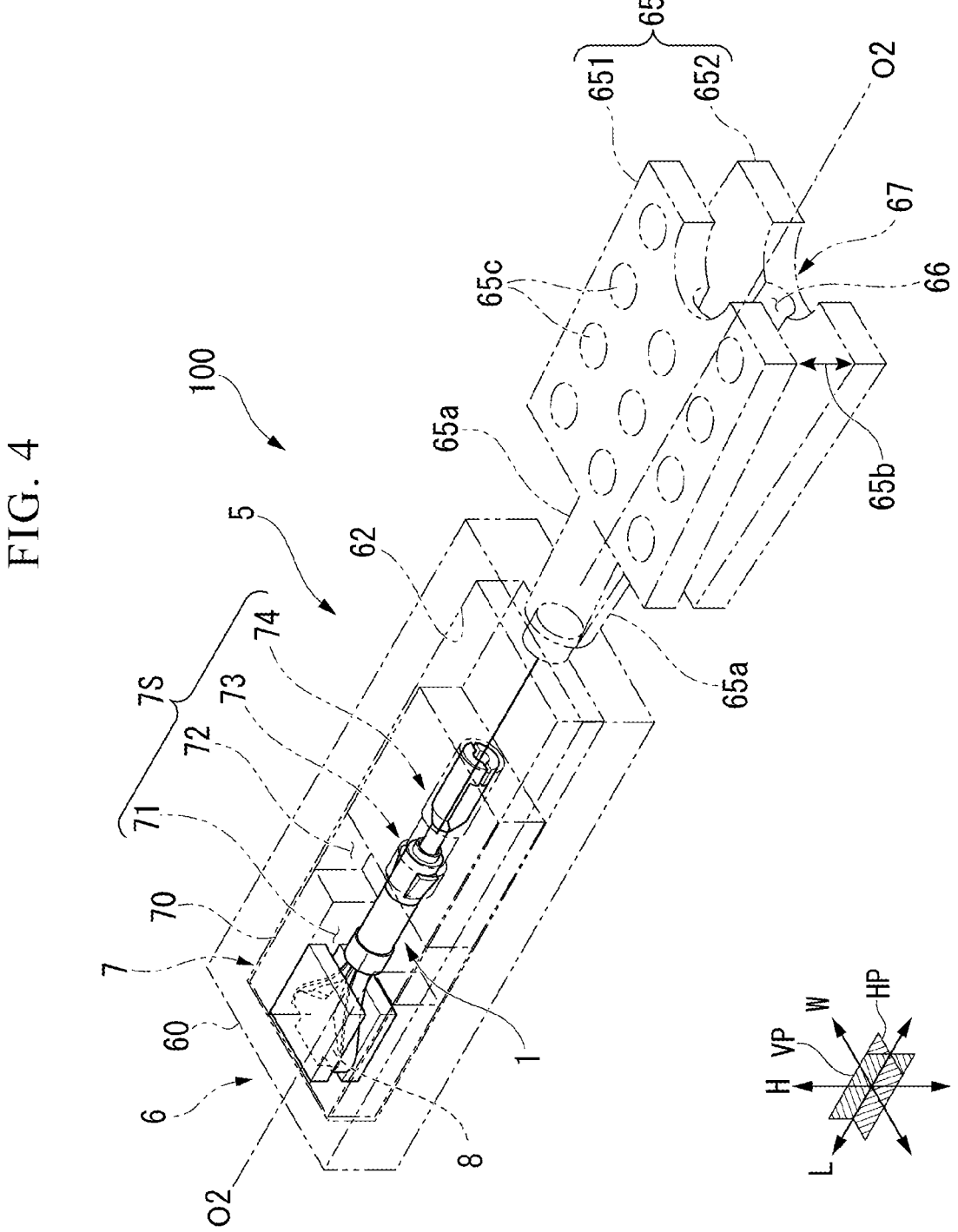
FIG. 4 is a perspective view of a cartridge in which the clip unit is stored.

FIG. 4 is a perspective view of the cartridge 5 in which the clip unit 1 is stored.

The cartridge 5 is a case in which the clip unit 1 is stored. The width of the cartridge 5 may range from about 10 mm to 20 mm, the length is about 50 mm, and the thickness may be about 5 mm, that is, the cartridge is formed in an easy-to-hold size.

The cartridge 5 may be manufactured, for example, by injection-molding a transparent resin material with an appropriate hardness such as ABS, PC, PP, PS, acryl, or cycloolefin polymers. Since the cartridge 5 is formed of a transparent resin material, a user can easily determine whether the clip unit 1 is present therein.

As illustrated in FIG. 4, one of two directions perpendicular to the length direction L of the cartridge 5 and perpendicular to each other is defined as a "width direction W," and the other is defined as a "height direction H." A plane parallel to the length direction L and the width direction W is defined as a "horizontal plane HP," and a plane parallel to the length direction L and the height direction H is defined as a "vertical plane VP." In the cartridge 5 in which the clip unit 1 is stored, the pair of arms 21 side is defined as a tip side L1 of the cartridge 5, and the connection member 4 side is defined as a base side L2 of the cartridge 5.

Figure 5:
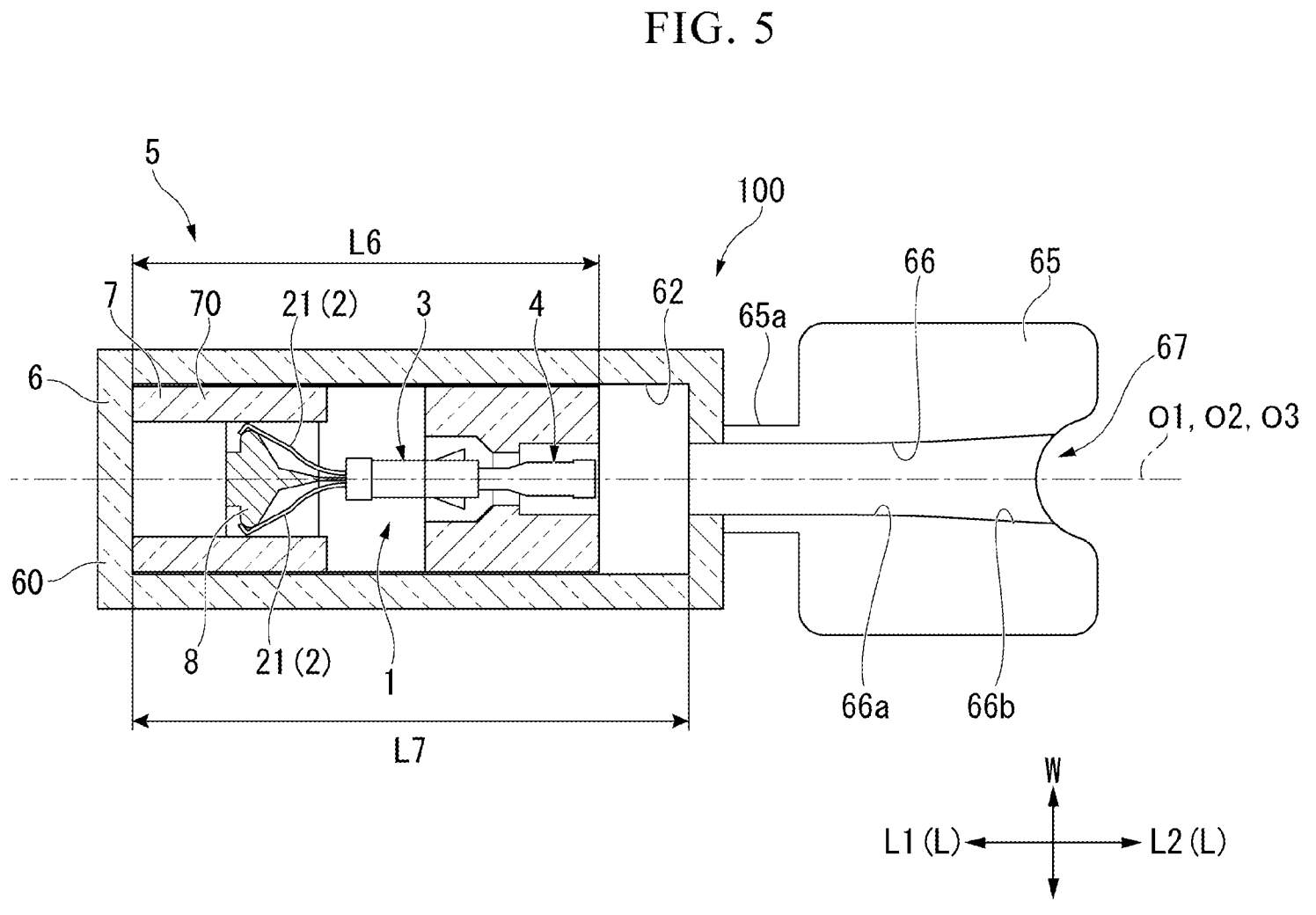

FIG. 5 is a sectional view of the cartridge 5 in which the clip unit 1 is stored.

The cartridge 5 may include a first cartridge 6, a second cartridge 7, and a regulation member 8. The regulation member 8 may be accommodated, located, or stored in the second cartridge 7. The second cartridge 7 may be accommodated, located, or stored in the first cartridge 6.

Figure 6:
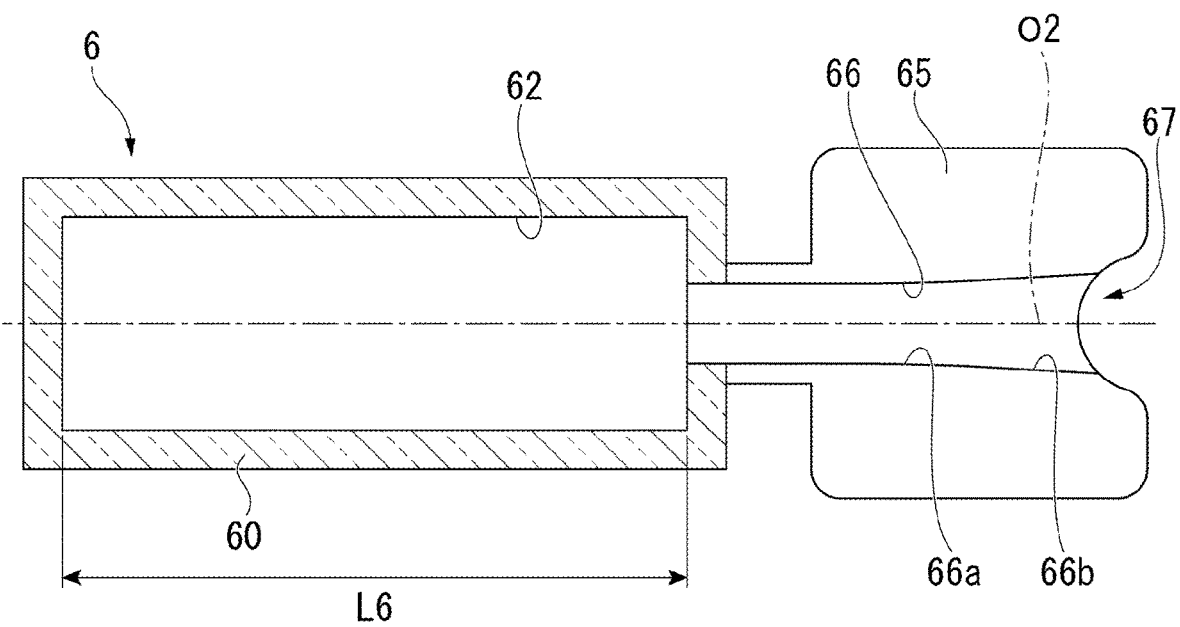
FIG. 6 is a sectional view of a first cartridge of the cartridge.

FIG. 6 is a sectional view of the first cartridge 6.

The first cartridge 6 may include a cartridge outer circumferential portion 60, a compression portion (plate) 65, and a sheath connection portion 66.

The cartridge outer circumferential portion 60 may be formed in a substantially rectangular box shape. A length in the width direction W of the cartridge outer circumferential portion 60 may be larger than a length in the height direction H of the cartridge outer circumferential portion 60. The cartridge outer circumferential portion 60 may include a second cartridge accommodation portion 62.

The second cartridge accommodation portion 62 may be formed in the cartridge outer circumferential portion 60. The second cartridge accommodation portion 62 may be formed in a substantially rectangular shape when seen or viewed in the height direction H. The second cartridge accommodation portion 62 may accommodate, hold, or store the second cartridge 7 such that the second cartridge 7 may be movable in the length direction L.

The compression portion 65 may be a plate-shaped member provided at the base end of the cartridge outer circumferential portion 60 as illustrated in FIG. 4. The compression portion 65 may include a first compression portion 651 and a second compression portion 652. The first compression portion 651 and the second compression portion 652 may be provided or arranged to face each other in the height direction H of the first cartridge 6.

The compression portion 65 may include a connection portion 65a connected to the cartridge outer circumferential portion 60. The connection portion 65a may separately connect the first compression portion 651 and the second compression portion 652 to the cartridge outer circumferential portion 60. The connection portion 65a may be bent such that the first compression portion 651 and the second compression portion 652 move away from each other. Accordingly, a gap 65b may be formed between the first compression portion 651 and the second compression portion 652. The first compression portion 651 and the second compression portion 652 may move farther away on the base side L2 than on the tip side L1.

The sheath connection portion 66 may be an insertion groove into which the sheath 220 can be inserted. The sheath connection portion 66 may be an arc-shaped groove formed in the inner surfaces of the first compression portion 651 and the second compression portion 652 and communicates with (e.g., connects to, contacts, touches, or the like) the second cartridge accommodation portion 62 in a storage area 7S. The sheath connection portion 66 may include a straight portion 66a with a diameter not changed and a tapered portion 66b with a diameter increasing toward an insertion port 67 on the base side L2.

A user can fix the sheath 220 to the first cartridge 6 by compressing the first compression portion 651 and the second compression portion 652 in a state in which the sheath 220 is inserted into the sheath connection portion 66 via the insertion port 67.

Figure 7:
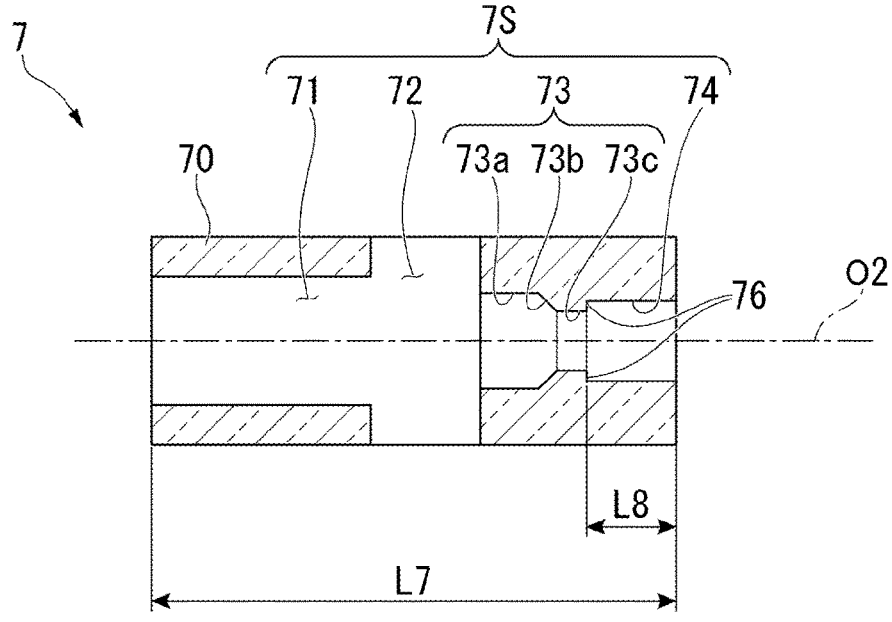
FIG. 7 is a sectional view of a second cartridge of the cartridge.

FIG. 7 is a sectional view of the second cartridge 7.

The second cartridge 7 may be formed in a substantially rectangular box shape and may be accommodated or located, or stored in the second cartridge accommodation portion 62 such that it may be movable forward and backward in the length direction L. A length L7 in the length direction L of the second cartridge 7 may be smaller than a length L6 in the length direction L of the second cartridge accommodation portion 62 of the first cartridge 6. The second cartridge 7 can move forward and backward in a range of a length (L6-L7) in the length direction L.

The second cartridge 7 may include a cartridge body 70 formed in a substantially rectangular box shape and a storage area 7S formed in the cartridge body 70.

The storage area 7S in which the clip unit 1 is stored such that the clip unit 1 is movable in the length direction (moving direction) L may be formed in the cartridge body 70. The storage area 7S may include a first area 71, a second area 72, a folded area 73, and a sheath insertion area 74. As illustrated in FIG. 7, the first area 71, the second area 72, the folded area 73, and the sheath insertion area 74 may be arranged from the tip side to the base side in the length direction L of the second cartridge 7. The first area 71, the second area 72, the folded area 73, and the sheath insertion area 74 may be internal spaces that are formed symmetric with respect to a vertical plane VP including the center axis O2 in the length direction L of the storage area 7S.

The second cartridge 7 may be accommodated, located, or stored in the second cartridge accommodation portion 62 such that the second cartridge 7 may be movable along the center axis O2 in the length direction L of the storage area 7S.

Figure 8:
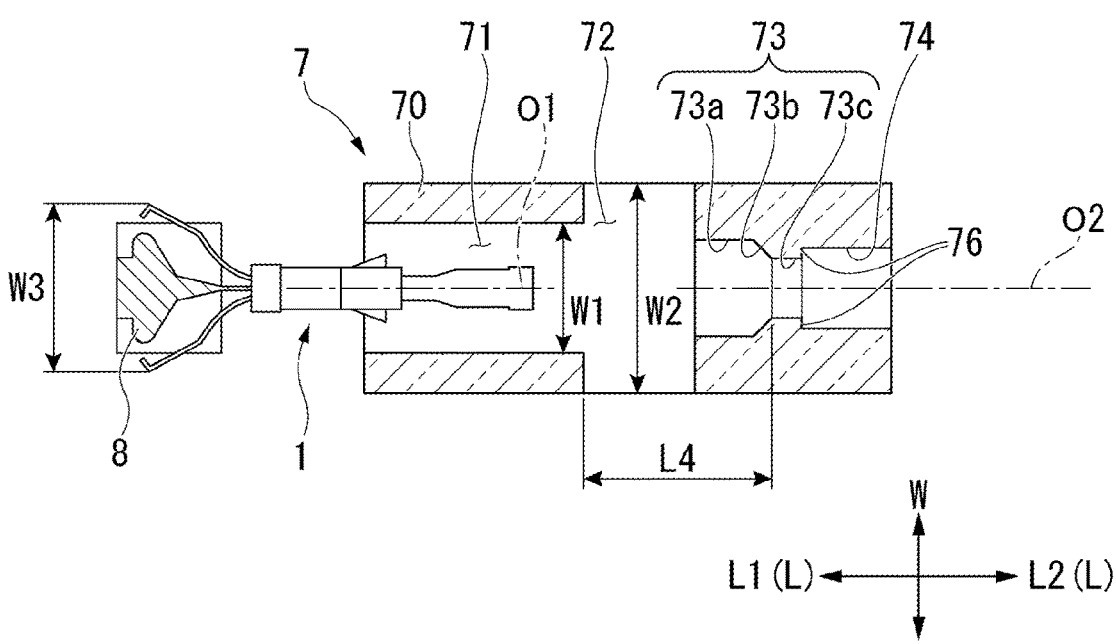
FIG. 8 is a diagram illustrating the clip unit which is stored in the second cartridge.

FIG. 8 is a diagram illustrating the clip unit 1 which is stored in the second cartridge 7.

The clip unit 1 may be stored in the storage area 7S such that the center axis O1 of the clip unit 1 is parallel to the length direction L of the second cartridge 7. The clip unit 1 may be stored in the storage area 7S such that the opening or closing direction P of a pair of arms 21 may match the width direction W of the second cartridge 7.

The first area 71 may be an internal space in which the clip unit 1 may be stored to be movable in the length direction L. The first area 71 may communicate with, contact, touch, or the like the second area 72.

The second area 72 may be an internal space in which the clip unit 1 may be stored to be movable in the length direction L. A length in the length direction L of the second area 72 may be smaller than a length in the length direction L of the first area 71. The second area 72 may communicate with, contact, touch, or the like the folded area 73.

As illustrated in FIG. 8, a length W1 in the width direction W of the first area 71 may be smaller than an opening width W3 of the pair of arms 21 in an open state. A length W2 in the width direction W of the second area 72 may be larger than the opening width W3 of the pair of arms 21 in the open state.

The folded area 73 may include a diameter-increased portion 73a, a tapered portion 73b, and a diameter-decreased portion 73c. The diameter-increased portion 73a, the tapered portion 73b, and the diameter-decreased portion 73c may be arranged from the tip side to the base side.

The diameter-increased portion 73a may be an area in which the elastic arm portion 44 of the connection member 4 may be allowed to be elastically expanded (opened and closed). In the diameter-increased portion 73a, the elastic arm portion 44 of the connection member 4 can be opened and closed in a direction perpendicular to the center axis O1 when the arrowhead-shaped hook portion 231 of the clip introduction device 200 engages with the connection member 4 of the clip unit 1.

The tapered portion 73b may be provided on the base side L2 of the diameter-increased portion 73a and may be formed in a taper shape. The tapered portion 73b may increase its diameter from the base side L2 to the tip side L1. Accordingly, when the presser tube 3 slides from the tip side L1 to the base side L2, the protruding or retracting wing 31 of the presser tube 3 may be accommodated, located, stored in the presser tube body 30.

The diameter-decreased portion 73c may be an area in which the protruding or retracting wing 31 may be maintained in the retracted state. The diameter-decreased portion 73c can maintain the elastic arm portion 44 in a state in which expanding of the elastic arm portion 44 of the connection member 4 may be prevented when the clip unit 1 is accommodated, located, or stored in the cartridge 5.

When the presser tube 3 slides in the tapered portion 73b from the tip side L1 to the base side L2, the protruding or retracting wing 31 of the presser tube 3 may become or enter the retracted state in which the protruding or retracting wing 31 can be accommodated, located, or stored in the sheath 220. Accordingly, the diameter-decreased portion 73c smoothly connected to the tapered portion 73b can maintain the protruding or retracting wing 31 of the presser tube 3 in the retracted state.

The sheath insertion area 74 may be an area into which the tip of the sheath 220 having passed through the sheath connection portion 66 may be inserted. The sheath insertion area 74 may be located on the base side L2 of the folded area 73 and may communicate with, connect to, contact, touch, or the like the folded area 73. In a part of the sheath insertion area 74 connected to the folded area 73, a length in the width direction W of the sheath insertion area 74 may be larger than a length in the width direction W of the folded area 73. A sheath contact portion 76 with which the distal tip 221 of the inserted sheath 220 can come into contact may be formed in the sheath insertion area 74.

A length L8 in the length direction L of the sheath insertion area 74 may be smaller than a difference (L6–L7) between the length L6 in the length direction L of the second cartridge accommodation portion 62 and the length L7 in the length direction L of the second cartridge 7 ((L6–L7)>L8).

Figure 9:
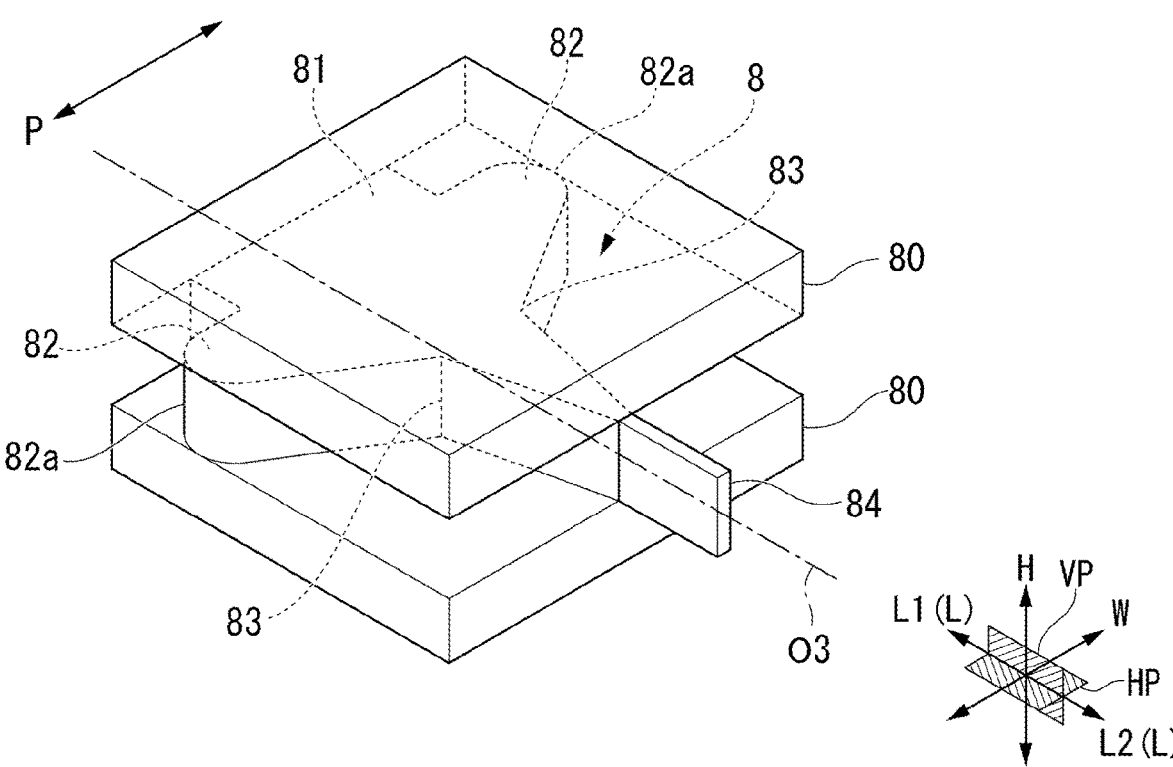
FIG. 9 is a perspective view of a regulation member of the cartridge.

FIG. 9 is a perspective view of the regulation member 8.

The regulation member 8 along with the clip unit 1 may be movably stored in the first area 71 and the second area 72. The regulation member 8 may be formed of, for example, the same resin material as the first cartridge 6 and the second cartridge 7. The regulation member 8 may not be formed of a transparent resin material unlike the first cartridge 6 and the second cartridge 7.

As illustrated in FIG. 9, the regulation member 8 may be formed in a shape symmetric with respect to the vertical plane VP including the center axis O3 in the length direction L. The regulation member 8 may include a tip portion 81, a protruding portion 82, a tapered portion 83, and a pushing portion 84. The tip portion 81, the protruding portion 82, the tapered portion 83, and the pushing portion 84 may be arranged from the tip side to the base side in the direction of the center axis O3 of the regulation member 8.

Figure 10:
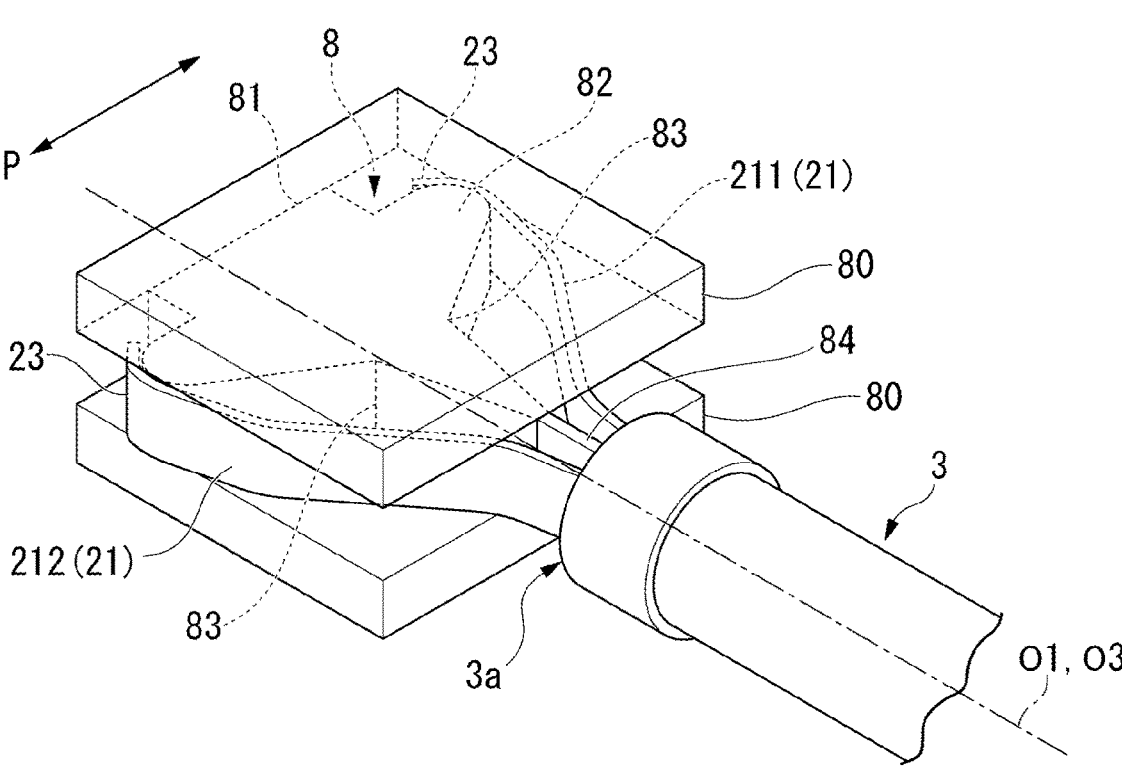
FIG. 10 is a perspective view of the regulation member which is grasped by a pair of arms.

FIG. 10 is a perspective view of the regulation member 8 which is grasped by a pair of arms 21.

The regulation member 8 may be grasped by the clip 2 such that the center axis O3 thereof substantially matches the center axis O1 of the clip unit 1. The clip unit 1 may be stored in the storage area 7S in a state in which the regulation member 8 is grasped by the clip 2 as illustrated in FIG. 5. At this time, the center axis O1, the center axis O2, and the center axis O3 may match.

The tip portion 81 may be provided on the tip side L1 to protrude from the protruding portion 82. The tip of the tip portion 81 may be located on the tip side more than the tissue grasping portion 23 of the clip 2 grasping the regulation member 8. Accordingly, the tip portion 81 may prevent the tissue grasping portion 23 of the clip 2 from coming into contact with the cartridge outer circumferential portion 60. The tip of the tip portion 81 may be formed in a plane perpendicular to the center axis O3.

The protruding portion 82 may be a member protruding in a direction (hereinafter referred to as a "protruding direction P") perpendicular to the center axis O3. The protruding portion 82 may be provided on both sides with the center axis O3 interposed therebetween. The protruding portion 82 may be grasped by the first arm 211 and the second arm 212. The opening or closing direction P of the pair of arms 21 grasping the protruding portion 82 may substantially match the protruding direction P of the protruding portion 82. The curvature of an outer circumferential surface of the protruding portion 82 may be smaller than the curvature of an inner circumferential surface of the tissue grasping portion 23. Accordingly, the pair of arms 21 can reliably grasp the protruding portion 82.

The tapered portion 83 may be a member that is formed in a taper shape. The tapered portion 83 may be provided on both sides with the center axis O3 interposed therebetween. The tapered portion 83 may be smaller in length in the protruding direction P than the protruding portion 82. The tapered portion 83 may decrease in length in the protruding direction P from the tip side L1 to the base side L2.

The pushing portion 84 may be a plate-shaped member that regulates a minimum approach distance between the clip 2 and the presser tube 3. The pushing portion 84 may be provided on the base side L2 of the tapered portion 83. The pushing portion 84 may engage with an edge of the tip opening 3a and thus be configured so it cannot intrude into the internal space of the presser tube 3 from the tip opening 3a. Accordingly, even when the clip 2 is pulled to approach the presser tube 3, the pushing portion 84 can regulate the minimum approach distance between the clip 2 and the presser tube 3 by engaging with the edge of the tip opening 3a.

As illustrated in FIG. 9, the regulation member 8 may be interposed or located between auxiliary members 80 in the height direction H. The auxiliary member 80 may adjust the position in the height direction H of the regulation member 8 such that the regulation member 8 may be grasped by the pair of arms 21. When the position in the height direction of the regulation member 8 does not need to be adjusted, the auxiliary members 80 are not necessary.

Figure 11:
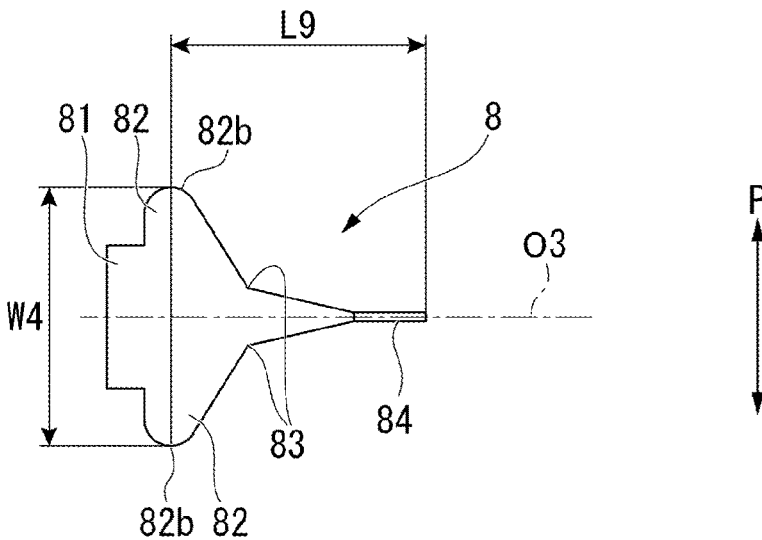
FIG. 11 is a plan view of the regulation member.

FIG. 11 is a plan view of the regulation member 8.

In the protruding portion 82, a part most protruding in the protruding direction P from the center axis O3 may be defined as a maximum protruding point 82b. A length W4 between the maximum protruding points 82b may be slightly smaller than the length W1 in the width direction W of the first area 71. A length in the length direction L from the maximum protruding point 82b to the base end of the pushing portion 84 is defined as a length L9.

Figure 12:
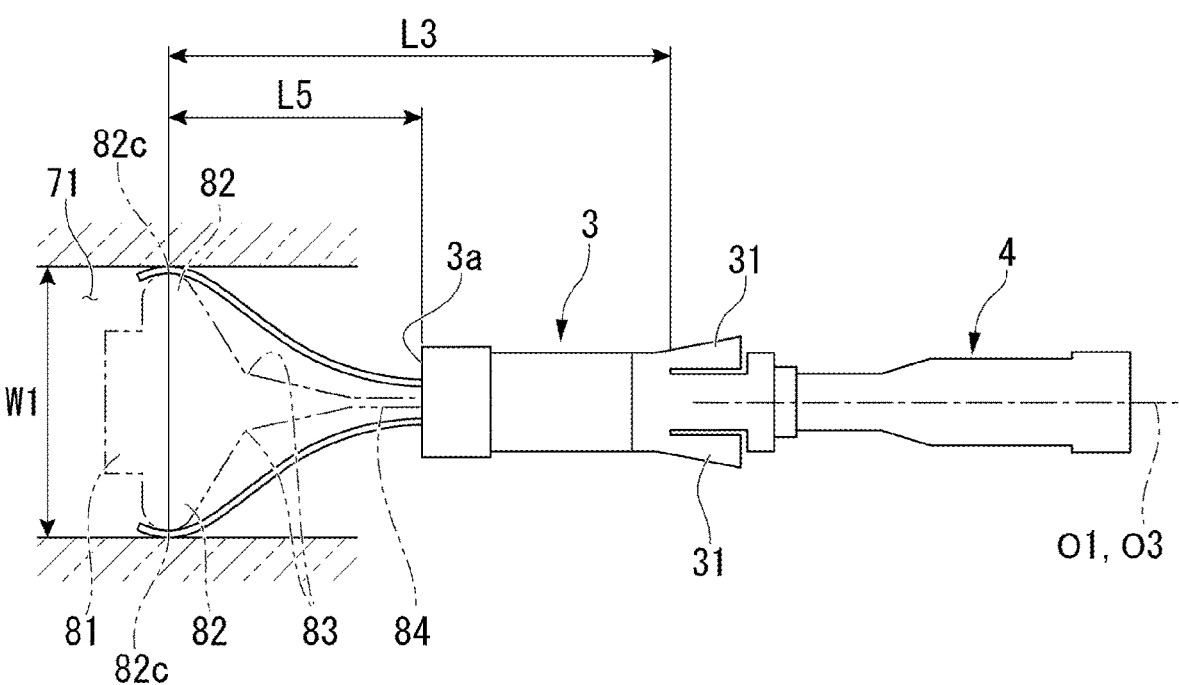
FIG. 12 is a plan view of the regulation member grasped in a first area.

FIG. 12 is a plan view of the regulation member 8 grasped in the first area 71.

The regulation member 8 may be stored in the first area 71 in a state in which it may be grasped by the pair of arms 21. The length W1 in the width direction W of the first area 71 may be smaller than the opening width W3 of the pair of arms 21 in the open state. Accordingly, the pair of arms 21 may grasp the regulation member 8 by switching from the open state to the closed state. The opening width of the pair of arms 21 may be about the length W1 in the width direction W of the first area 71. The pair of arms 21 may come into contact with the cartridge body 70 in the opening or closing direction P. A length in the length direction L from a contact point 82c between the pair of arms 21 and the cartridge body 70 to the base end of the pushing portion 84 is defined as a length L5.

The length L5 in the direction of the center axis O3 from the contact point 82c to the base end of the pushing portion 84 may be equal to or greater than the length L9 in the direction of the center axis O3 from the maximum protruding point 82b to the base end of the pushing portion 84. In such an example, the clip 2 may engage surely or securely with the regulation member 8 and can be pulled to the base side L2 when the clip 2 is pulled to the base side L2.

As illustrated in FIGS. 11 and 12, the length W4 between the maximum protruding points 82b may be slightly smaller than the length W1 in the width direction W of the first area 71. Accordingly, the state in which the regulation member 8 is grasped by the pair of arms 21 in the first area 71 may be maintained.

The length L3 (see FIG. 12) in the length direction L from the contact point 82c to the tip of the protruding/retracting wing 31 may be equal to or greater than the length L4 (see FIG. 8) in the length direction L from the tip of the second area 72 to the base end of the tapered portion 83b.

The operations of the cartridge system 100 will be described below. FIGS. 13 to 21 are diagrams illustrating a method of loading the clip unit 1 into the clip introduction device 200 using the cartridge 5.

Figure 13:
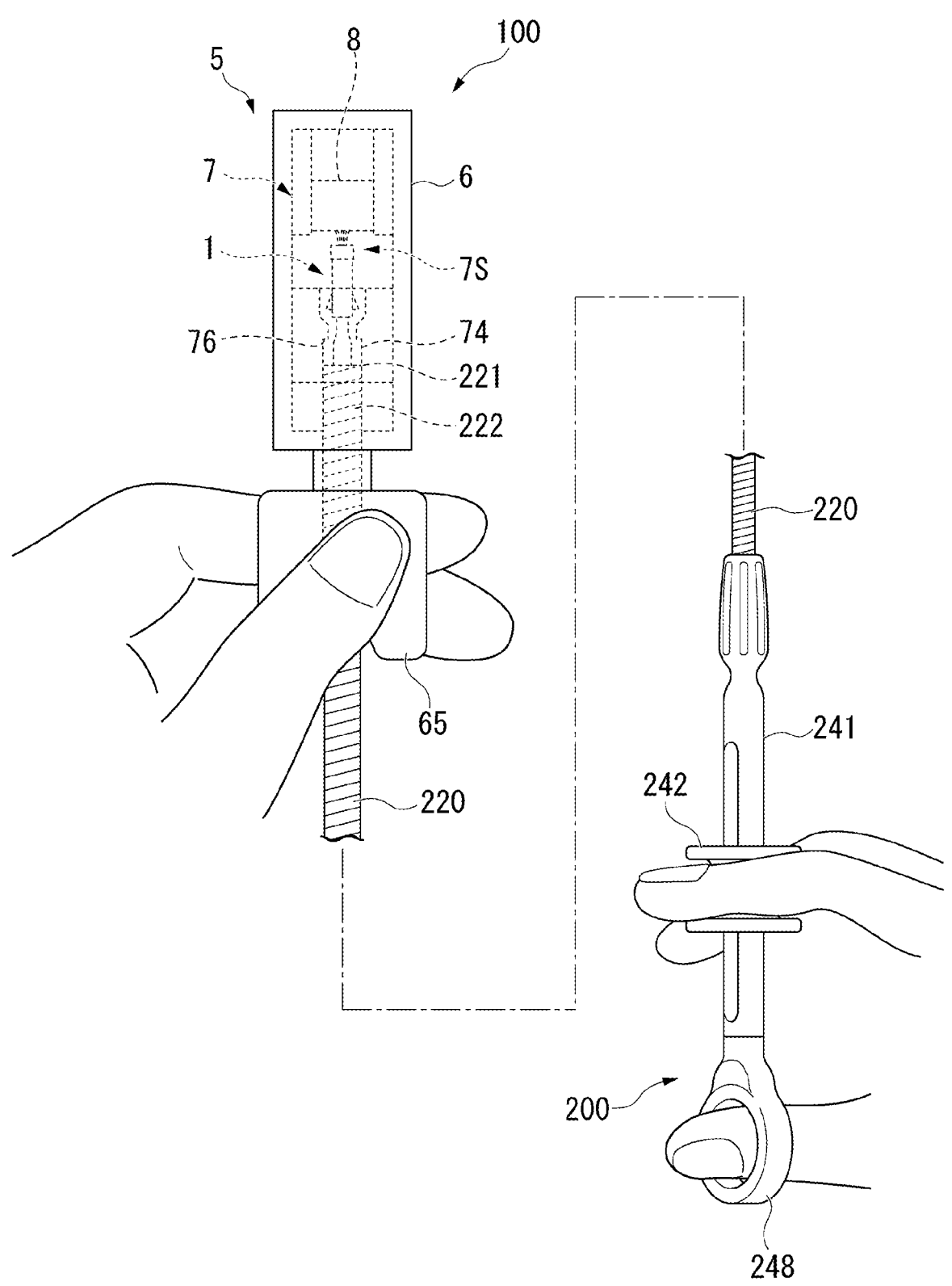
FIG. 13 is a diagram illustrating a method of loading the clip unit into the clip introduction device using the cartridge.

FIG. 13 is a diagram illustrating an operation of loading the clip unit 1.

A user may insert the sheath 220 into the sheath insertion area 74 via the insertion port 67. The distal tip 221 of the sheath 220 illustrated in FIG. 13 does not come into contact with the sheath contact portion 76 of the sheath insertion area 74. The user may fixe the sheath 220 to the first cartridge 6 by compressing the sheath 220 with the compression portion 65.

Figure 14:
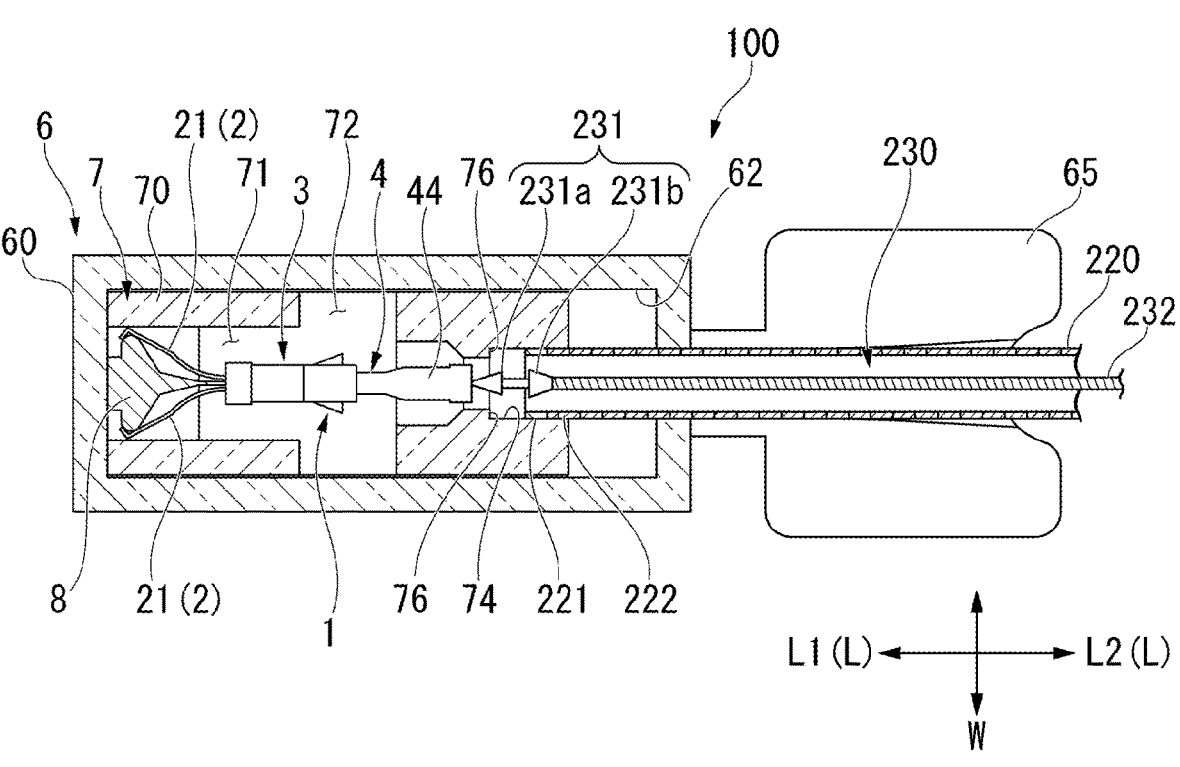
FIG. 14 is a diagram illustrating a method of loading the clip unit into the clip introduction device using the cartridge.

FIG. 14 is a diagram illustrating the clip unit 1 which is connected to the clip introduction device 200.

By moving the slider 242 relative to the operation portion body 241 of the operation portion 240 and moving the operating wire 230 relative to the sheath 220, the user may press the connection member 4 with the arrowhead-shaped hook portion 231 and move the regulation member 8 and the clip unit 1 forward until the regulation member 8 comes into contact with the cartridge outer circumferential portion 60.

Figure 15:
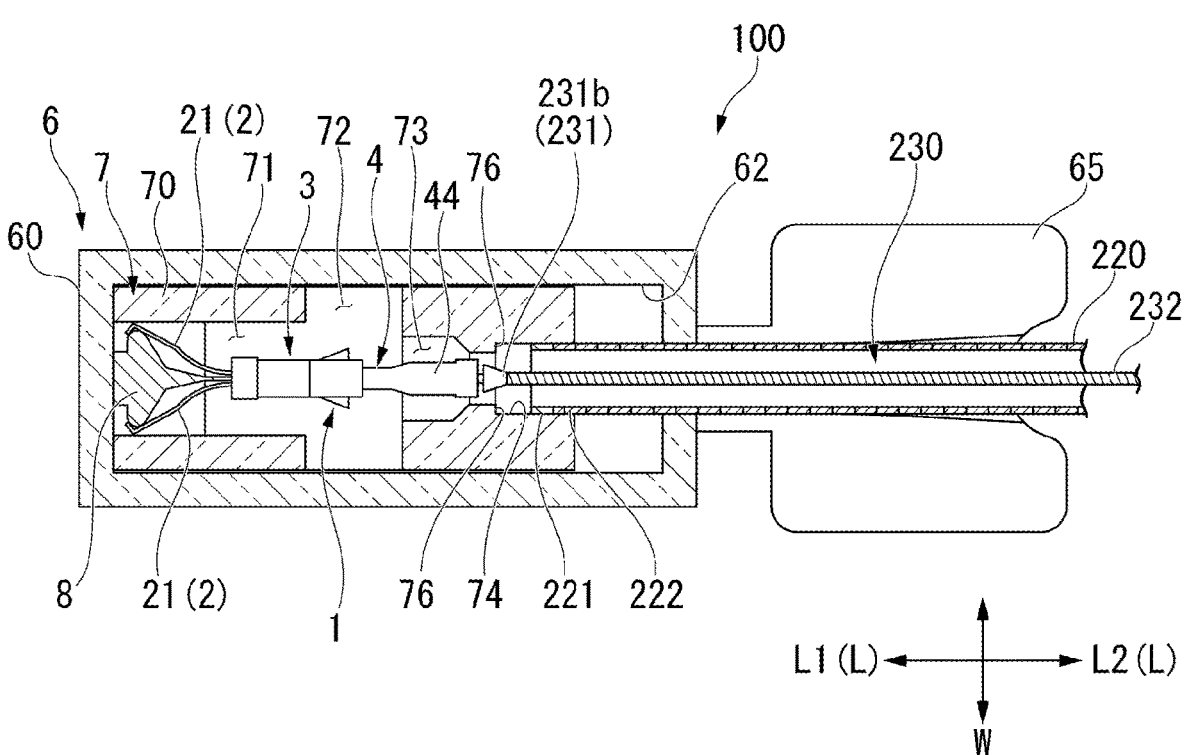
FIG. 15 is a diagram illustrating a method of loading the clip unit into the clip introduction device using the cartridge.

FIG. 15 is a diagram illustrating the clip unit 1 which is connected to the clip introduction device 200.

The user may connect the engagement portion 231a of the arrowhead-shaped hook portion 231 to the elastic arm portion 44 of the connection member 4 by further moving the arrowhead-shaped hook portion 231 forward.

The tip of the tip portion 81 of the regulation member 8 may be formed in the plane perpendicular to the center axis O3. Accordingly, even when the tip of the clip unit 1 pressed to the tip side L1 by the arrowhead-shaped hook portion 231 comes into contact with the cartridge outer circumferential portion 60, the center axis O1 of the clip unit 1 is difficult to depart from the center axis O2 of the storage area 7S.

Figure 16:
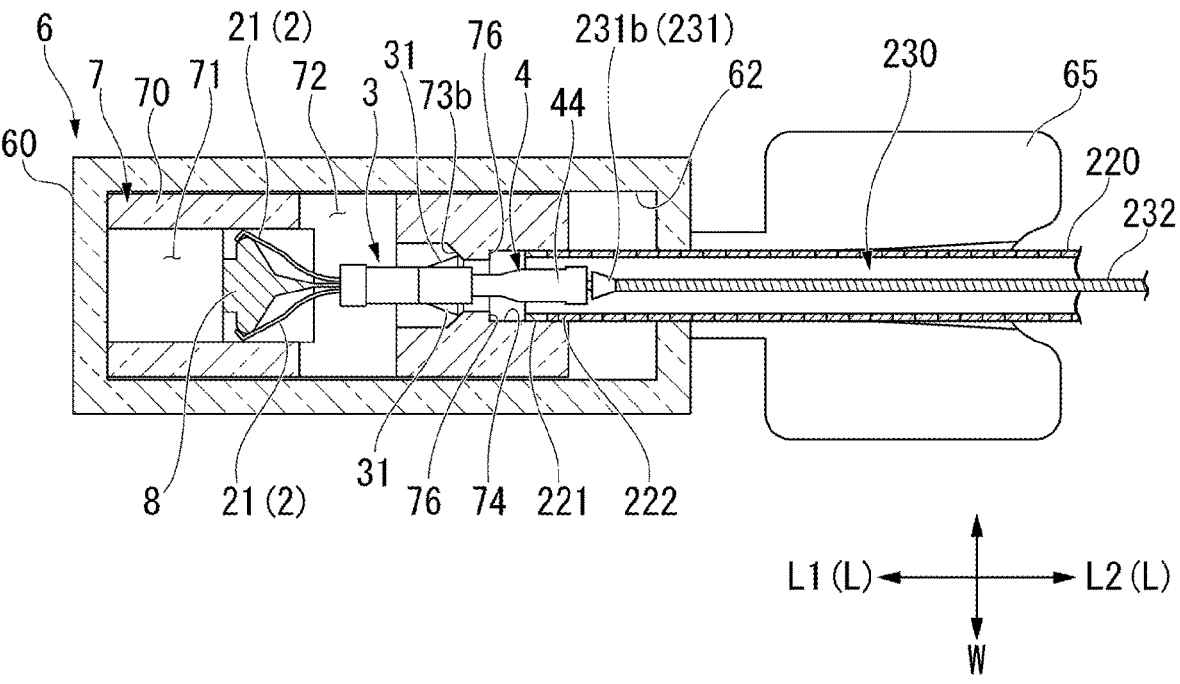
FIG. 16 is a diagram illustrating a method of loading the clip unit into the clip introduction device using the cartridge.

As illustrated in FIG. 16, the user may pull the operating wire 230. The clip 2 of the clip unit 1 may be pulled to the base side L2 by the connection member 4 connected to the arrowhead-shaped hook portion 231. The hook 41f of the connection member 4 may pull the connection portion 22 of the clip 2 without being broken. The regulation member 8 may move in the first area 71 of the storage area 7S in a state in which it is in contact with the pair of arms 21. In such an example, since the pair of arms 21 having a self-expanding force engages with the edge of the tip opening 3a of the presser tube 3, the presser tube 3 along with the clip 2 can also be pulled to the base side L2.

The pair of arms 21 may come into contact with the cartridge body 70 in the opening or closing direction P in the first area 71. It is possible to appropriately prevent the clip 2 from being pulled into the internal space of the presser tube 3 and being locked in the closed state by the presser tube 3 due to a frictional force generated by contact between the pair of arms 21 and the cartridge body 70.

When the clip 2 is pulled to the base side L2, the pushing portion 84 of the regulation member 8 may engage with the edge of the tip opening 3a of the presser tube 3 and thus the minimum approach distance between the clip 2 and the presser tube 3 may 3 may be regulated. The pushing portion 84 may come into contact with the presser tube 3 in a state in which it is in contact with the pair of arms 21 by pulling the operating wire 230 and may regulate movement of the regulation member 8 relative to the presser tube 3. Accordingly, it is also possible to appropriately prevent the clip 2 being pulled to the base side L2 by the connection member 4 from being pulled into the internal space of the presser tube 3 and being locked in the closed state by the presser tube 3.

Figure 17:
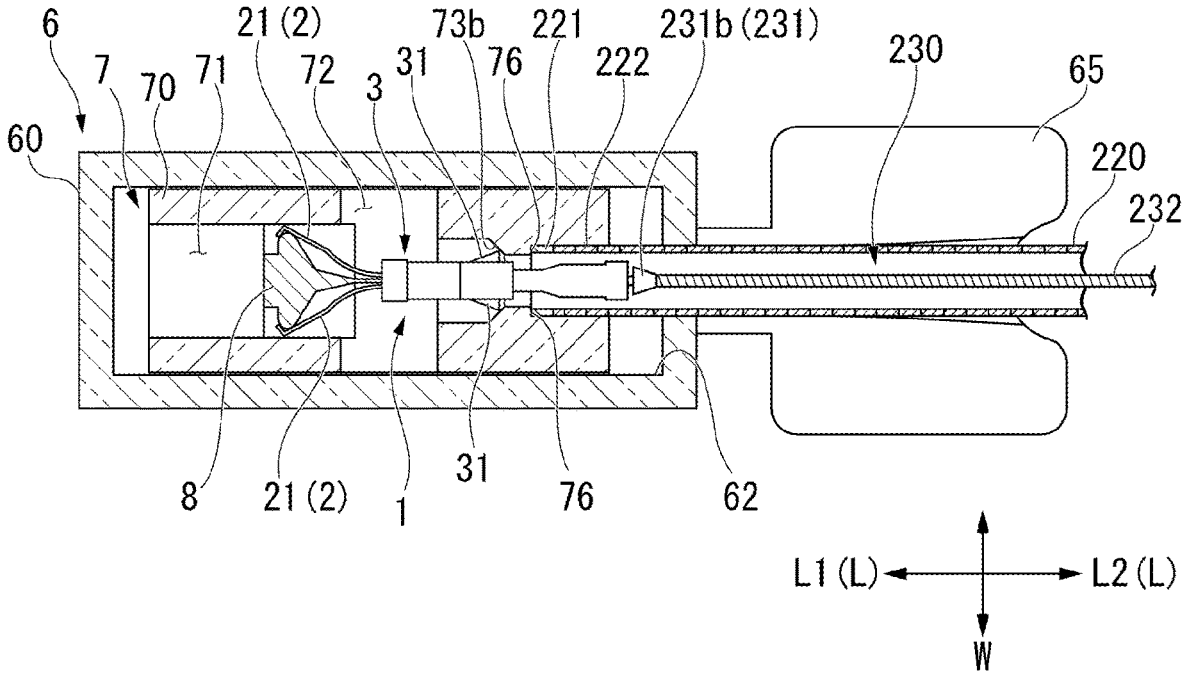
FIG. 17 is a diagram illustrating a method of loading the clip unit into the clip introduction device using the cartridge.

As illustrated in FIG. 17, the user may further pull the clip unit 1 to the base side L2. Since the protruding or retracting wing 31 of the presser tube 3 of the clip unit 1 engages with the tapered portion 73b, the second cartridge 7 along with the clip unit 1 can be pulled to the base side L2. As described above, the length L8 in the length direction L of the sheath insertion area 74 may be smaller than the difference between the length L6 and the length L7 ((L6–L7)>L8). Accordingly, the second cartridge 7 can be pulled to the base side L2 until the distal tip 221 of the sheath 220 inserted into the sheath insertion area 74 comes into contact with the sheath contact portion 76.

Figure 18:
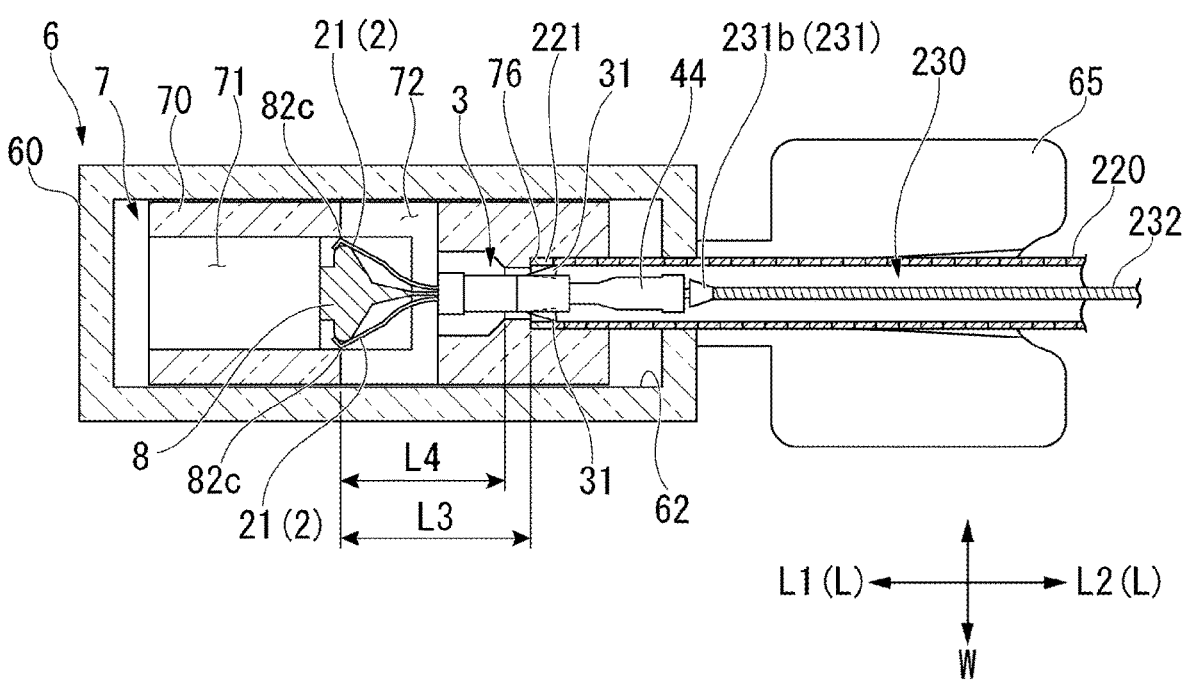
FIG. 18 is a diagram illustrating a method of loading the clip unit into the clip introduction device using the cartridge.

The user may further pull the clip unit 1 to the base side L2. As illustrated in FIG. 18, the presser tube 3 may pass through the folded area 73. When the presser tube 3 slides in the folded area 73 from the tip side L1 to the base side L2, the protruding or retracting wing 31 of the presser tube 3 can become or enter the retracted state in which it can be accommodated, located, or stored in the sheath 220. The protruding or retracting wing 31 maintained in the retracted state may be pulled into the sheath 220. The protruding or retracting wing 31 pulled into the sheath 220 may be maintained in the retracted state.

The distal tip 221 of the sheath 220 may be in contact with the sheath contact portion 76 and thus almost no gap in the length direction L can be formed between the distal tip 221 and the sheath contact portion 76. Accordingly, the protruding or retracting wing 31 of the presser tube 3 may be smoothly accommodated, located, or stored in the sheath 220.

As illustrated in FIG. 18, the length L3 in the length direction L from the contact point 82c to the tip of the protruding or retracting wing 31 may be equal to or greater than the length L4 in the length direction L from the tip of the second area 72 to the base end of the tapered portion 73b. Accordingly, when the protruding or retracting wing 31 of the presser tube 3 is accommodated, located, or stored in the presser tube 3, the contact points 82c between the pair of arms 21 and the cartridge body 70 may be located in the first area 71. That is, until the protruding or retracting wing 31 becomes or enters the retracted state, the pair of arms 21 grasp the regulation member 8 and is not pulled into the internal space of the presser tube 3.

Figure 19:
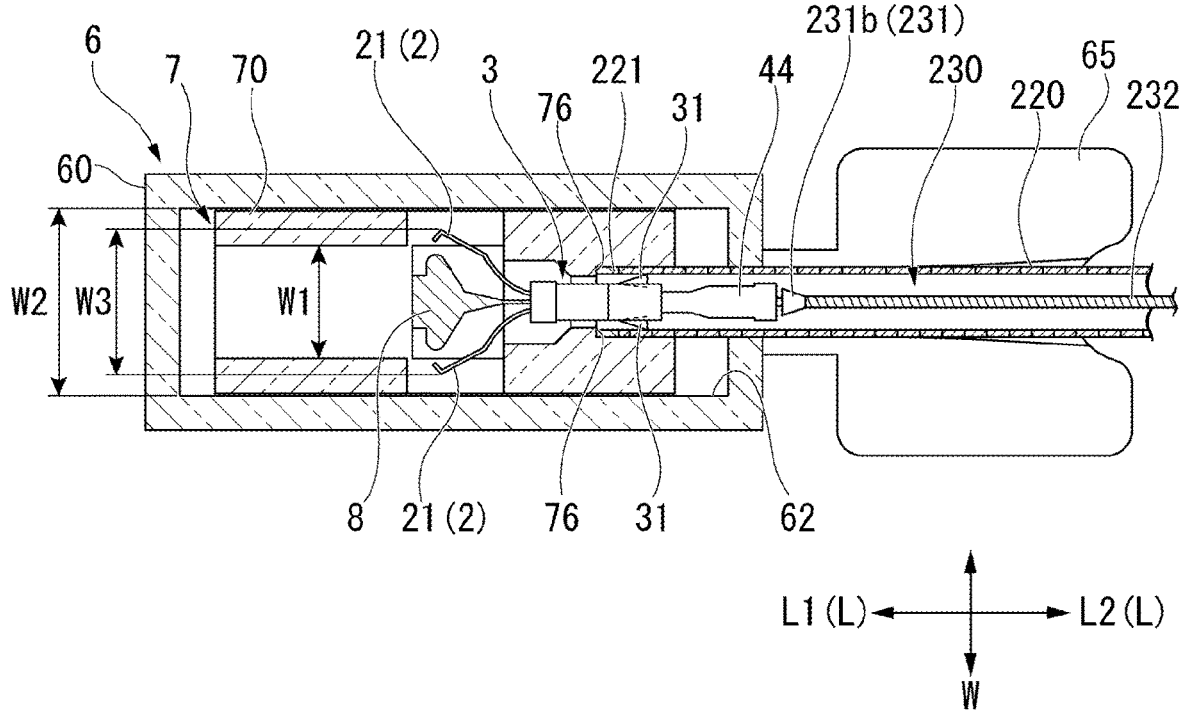
FIG. 19 is a diagram illustrating a method of loading the clip unit into the clip introduction device using the cartridge.

As illustrated in FIG. 19, the user may further pull the operating wire 230 and pulls the regulation member 8 to the second area 72. The length W2 in the width direction W of the second area 72 may be larger than the opening width W3 of the pair of arms 21 in the open state. Accordingly, the regulation member 8 is not grasped by the pair of arms 21 in the second area 72.

Figure 20:
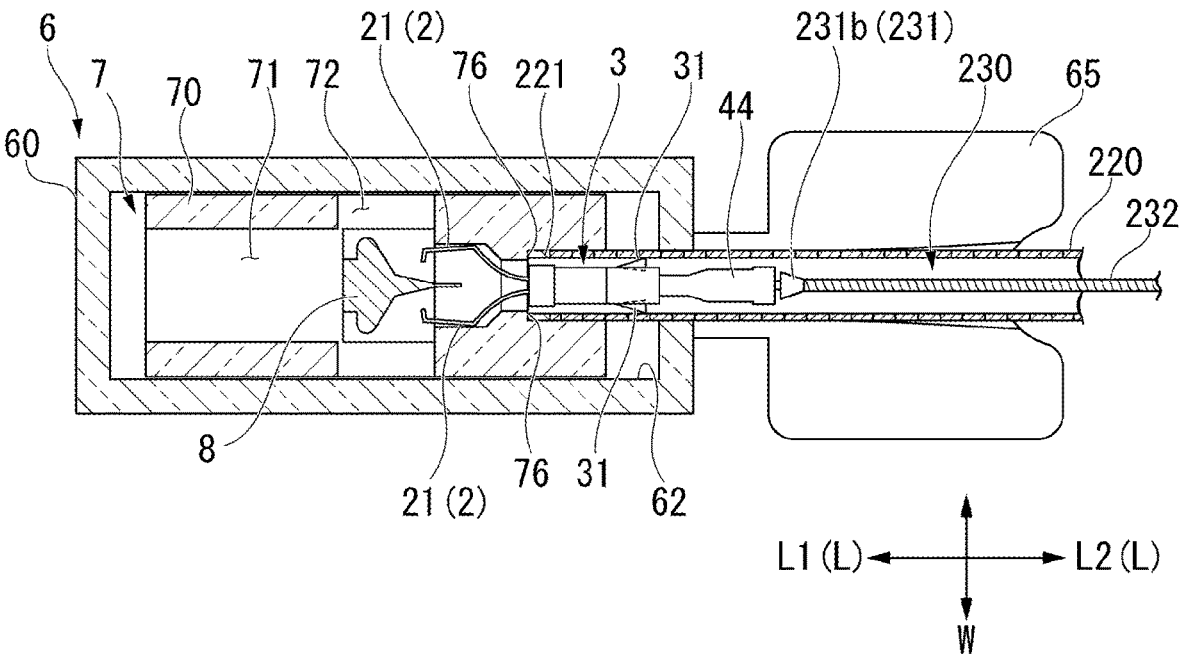
FIG. 20 is a diagram illustrating a method of loading the clip unit into the clip introduction device using the cartridge.

As illustrated in FIG. 20, the user further pulls the operating wire 230. The clip 2 may be detached from the regulation member 8 and may be pulled to the base side L2. In the regulation member 8, the tapered portion 83 may be formed on the base side L2 of the protruding portion 82 grasped by the pair of arms 21. Accordingly, when the regulation member 8 is pulled to the base side L2, it is difficult for the pair of arms 21 to be hooked to the regulation member 8.

Figure 21:
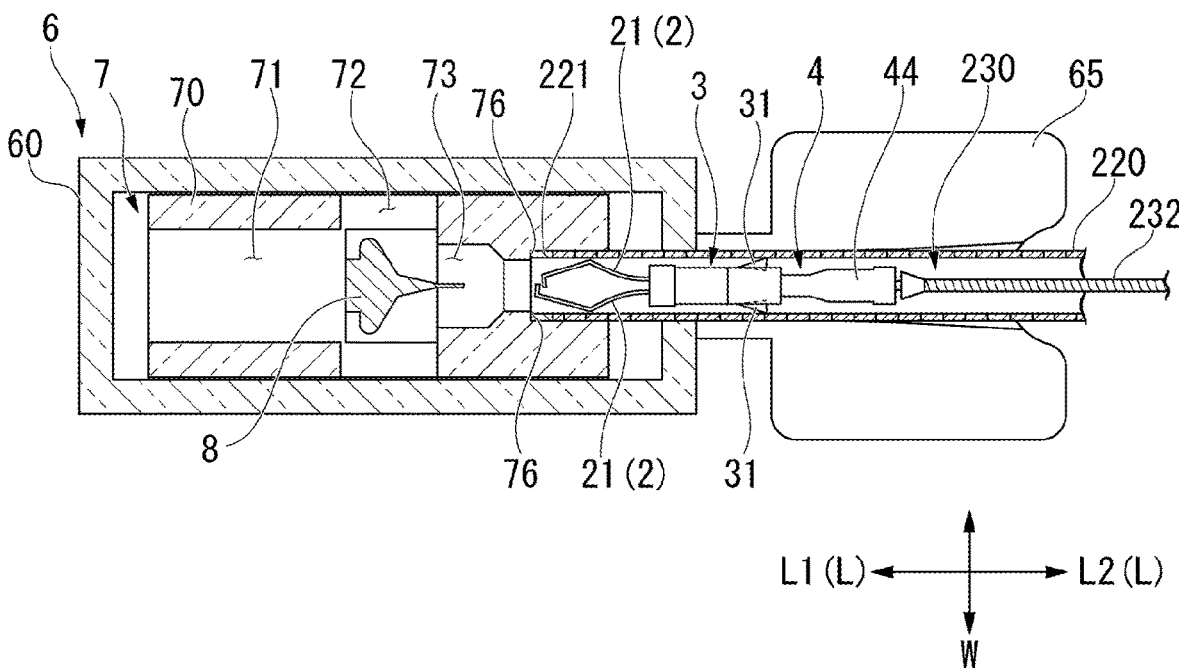
FIG. 21 is a diagram illustrating a method of loading the clip unit into the clip introduction device using the cartridge.

As illustrated in FIG. 21, the user may further pull the operating wire 230. Since the pair of arms 21 does not grasp the regulation member 8, the minimum approach distance between the clip 2 and the presser tube 3 is not regulated. The clip 2 may be pulled to the base side L2 and may be pulled into the internal space of the presser tube 3 and pulled into the sheath 220. The clip 2 may be pulled into the sheath 220 without being pulled into the internal space of the presser tube 3. As a result, loading of the clip unit 1 into the clip introduction device 200 is completed. The user may decompress the sheath 220 with the compression portion 65 and may take out or remove the sheath 220 from the cartridge 5.

Operations and Functions of Clip Unit 1

Operations and functions of the clip unit 1 will be described below with reference to FIGS. 22 to 26.

The connection member 4 of the loaded clip unit 1 may be connected to the arrowhead-shaped hook portion 231 inserted into the sheath 220 as illustrated in FIG. 21. The protruding or retracting wing 31 may be pressed into the retracted state by the inner circumferential surface of the sheath 220.

The pair of arms 21 of the loaded clip unit 1 may be pressed into the closed state by the inner circumferential surface of the sheath 220. The engagement portion 24 may 24 may be located on the tip side of the base opening 3*b*, and the pair of arms 21 are not locked in the closed state.

Figure 22:
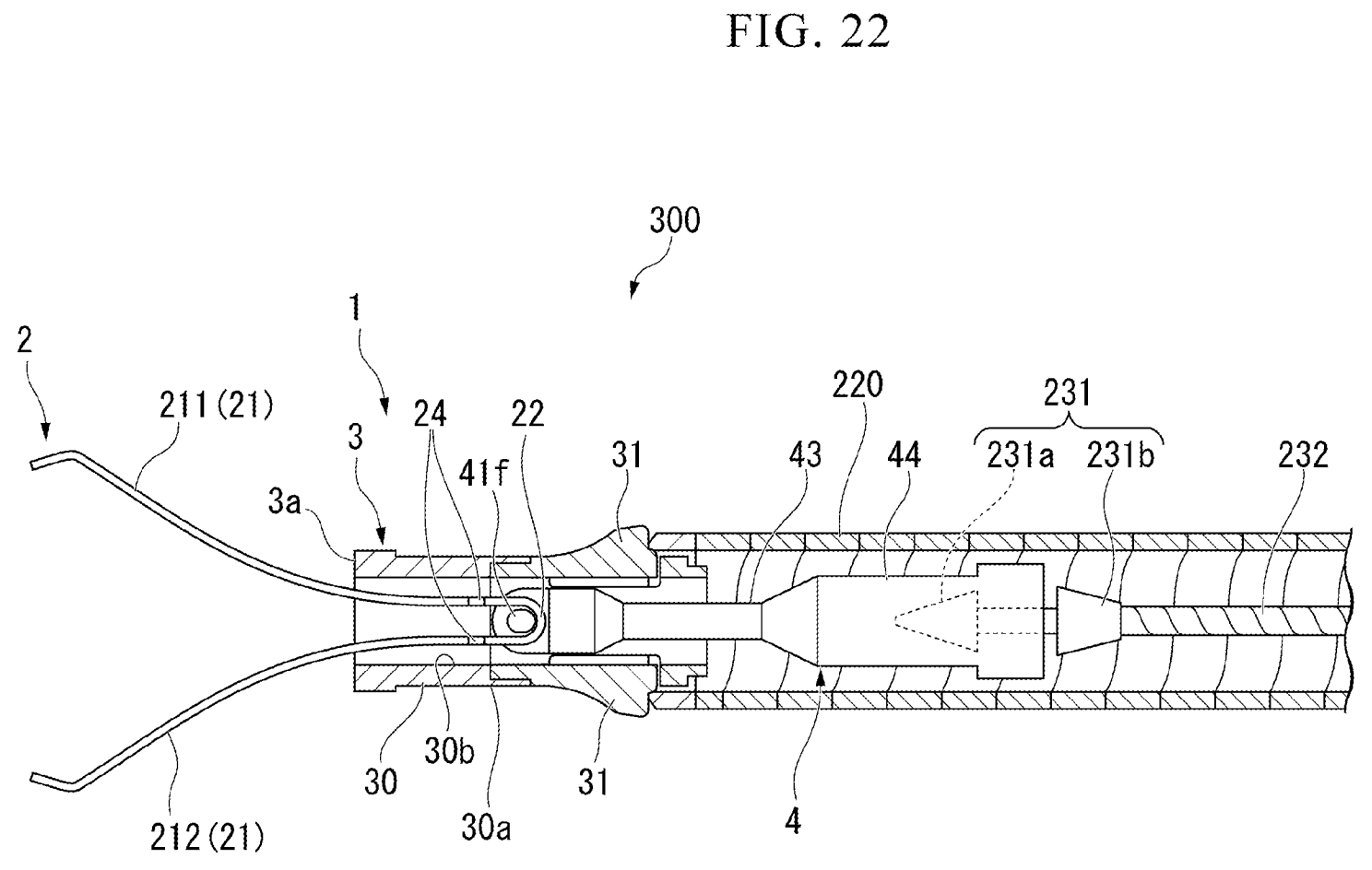

FIG. 22 is a diagram illustrating the clip unit 1 introduced into a body.

A user may introduce the clip unit 1 loaded into the sheath 220 into a body via a channel of an endoscope. The user may move the arrowhead-shaped hook portion 231 forward by moving the slider 242 forward along the operation portion body 241. The user can move the clip unit 1 forward until the protruding or retracting wing 31 gets out of or exits the sheath 220. When the protruding or retracting wing 31 exits the sheath 220, the protruding or retracting wing 31 returns from the retracted state to the protruded state which is a basic posture.

When the tips of the pair of arms 21 exit the sheath 220, the clip 2 returns to the open state while moving to the tip side A1 relative to the presser tube 3 with a self-expanding force of the pair of arms 21 as a restoring force. Even when the pair of arms 21 returns to the open state and protrudes most from the presser tube 3, the engagement portion 24 may be disposed in the internal area of the presser tube 3.

Figure 23:
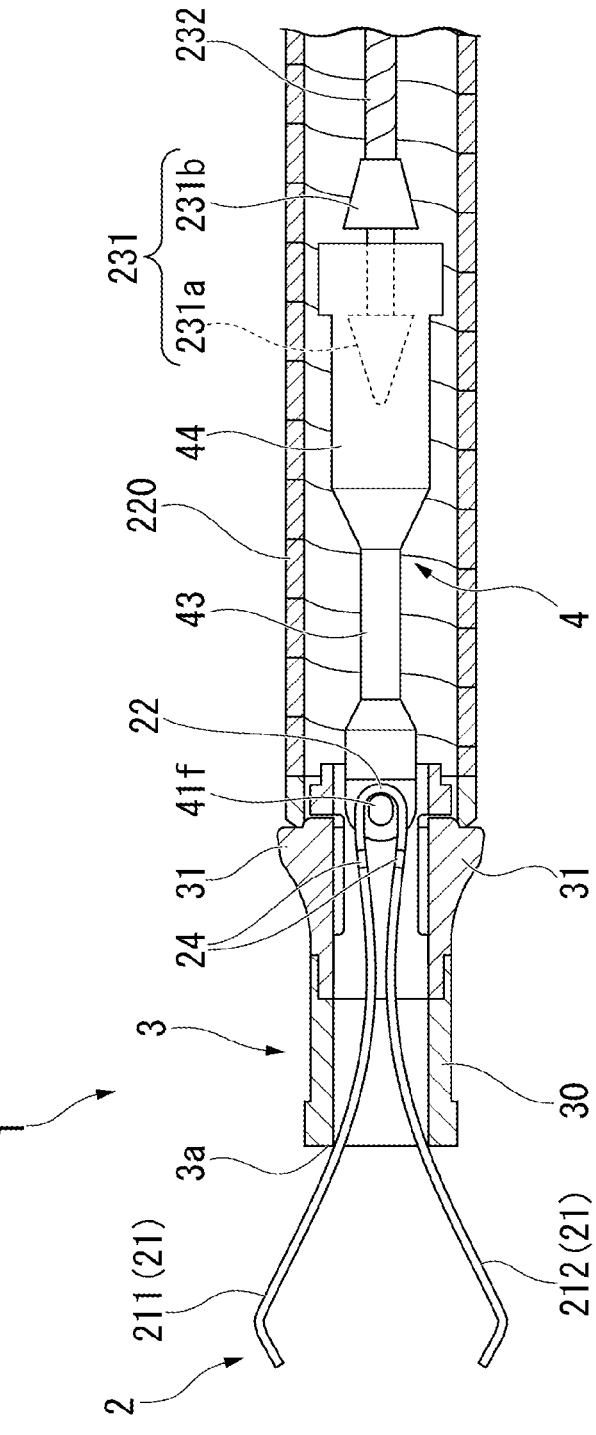
FIG. 23 is a diagram illustrating the clip unit in which a pair of arms is closed.

FIG. 23 is a diagram illustrating the clip unit 1 in which a pair of arms 21 is closed.

The user may move the arrowhead-shaped hook portion 231 backward by moving the slider 242 backward along the operation portion body 241. The connection member 4 may be connected to the arrowhead-shaped hook portion 231 pulls the clip 2. The pair of arms 21 with a self-expanding force may be pulled to the base side A2 and thus presses the tip opening 3*a* of the presser tube to the base side A2. The protruding or retracting wing 31 in the protruded state may engage with the sheath 220 and thus is not pulled into the sheath 220. Accordingly, the clip 2 pulled by the connection member 4 may be pulled into the presser tube 3.

When the connection portion 22 of the clip 2 is pulled to the base side A2 of the presser tube 3 by the connection member 4, the pair of arms 21 is pulled into the presser tube 3, and the pair of arms 21 is gradually closed. When the pulling force of the connection portion 22 is released in this state, the clip 2 returns to the open state while moving to the tip side A1 with the self-expanding force of the pair of arms

21 as a restoring force. The user can return the pair of arms 21 to the open state and re-grasp tissue.

Figure 24:
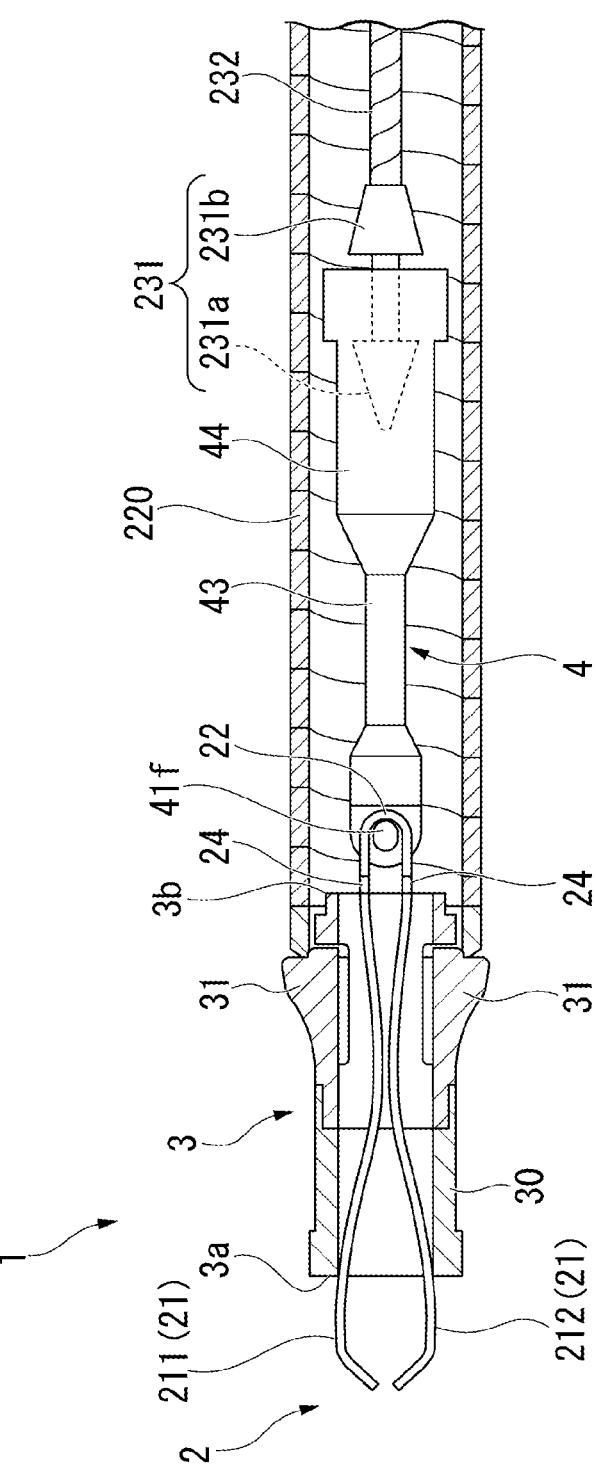
FIG. 24 is a diagram illustrating the clip unit in which a clip has been locked.

FIG. 24 is a diagram illustrating the clip unit 1 of which the clip 2 has been locked.

When the connection portion 22 is further pulled to the base side A2 of the presser tube 3, the engagement portion 24 is pulled to the base side from the base opening 3*b*. Since the connection portion 22 side of the engagement portion 24 is formed as a slope with an obtuse angle, the engagement portion 24 can be easily pulled to the base side A2 from the base opening 3*b*. On the other hand, since the tissue grasping portion 23 side of the engagement portion 24 is formed as a slope with an acute angle, the engagement portion 24 and the base opening 3b can engage with each other when the engagement portion 24 is pulled to the base side from the base opening 3*b*. As a result, movement of the clip 2 to the tip side relative to the presser tube 3 can be regulated, and the pair of arms 21 can be locked in the closed state. When the pair of arms 21 is locked in the closed state, the pair of arms 21 cannot return to the open state.

Figure 25:
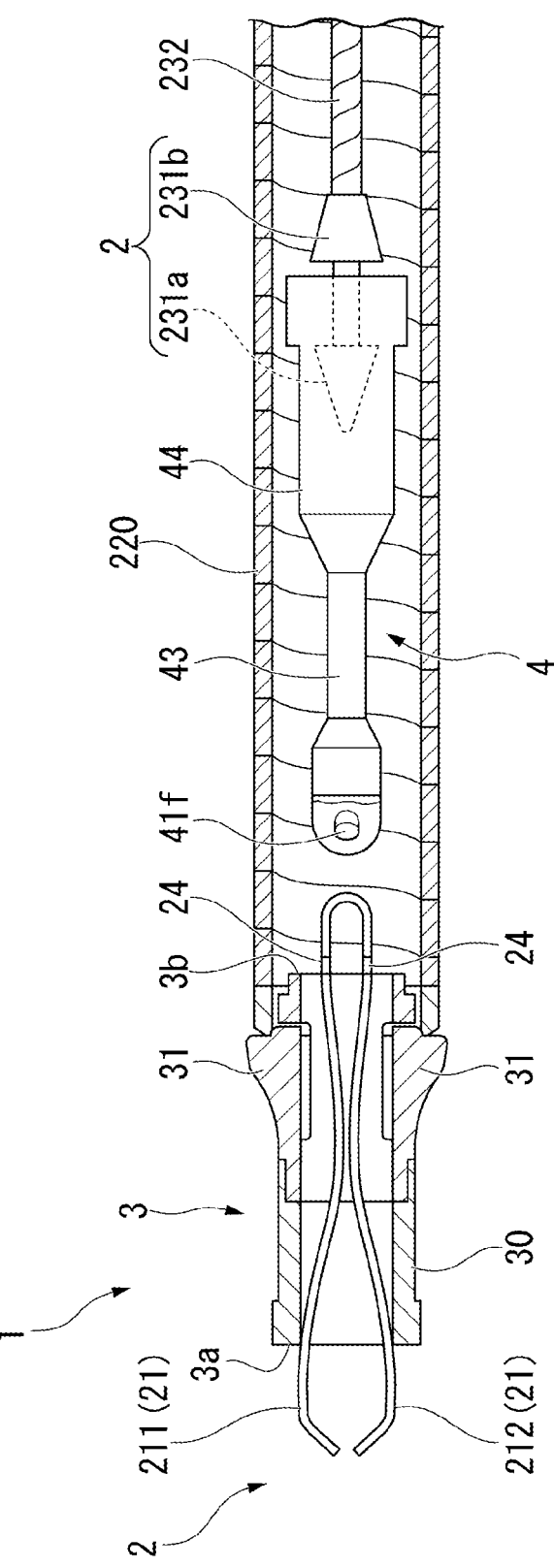
FIG. 25 is a diagram illustrating the clip unit in which the clip has been unlocked.

FIG. 25 is a diagram illustrating the clip unit 1 from which the clip 2 has been detached.

The user may further pull the clip 2. For example, when a breaking force based on pulling of 20 N to 90 N is applied to the hook 41*f*, the breakable portion 41*b* is broken. The breaking strength of the breakable portion 41*b* may be lower than the breaking strength of the connection portion body 43. Accordingly, the breakable portion 41*b* instead of the connection portion body 43 is broken.

Figure 26:
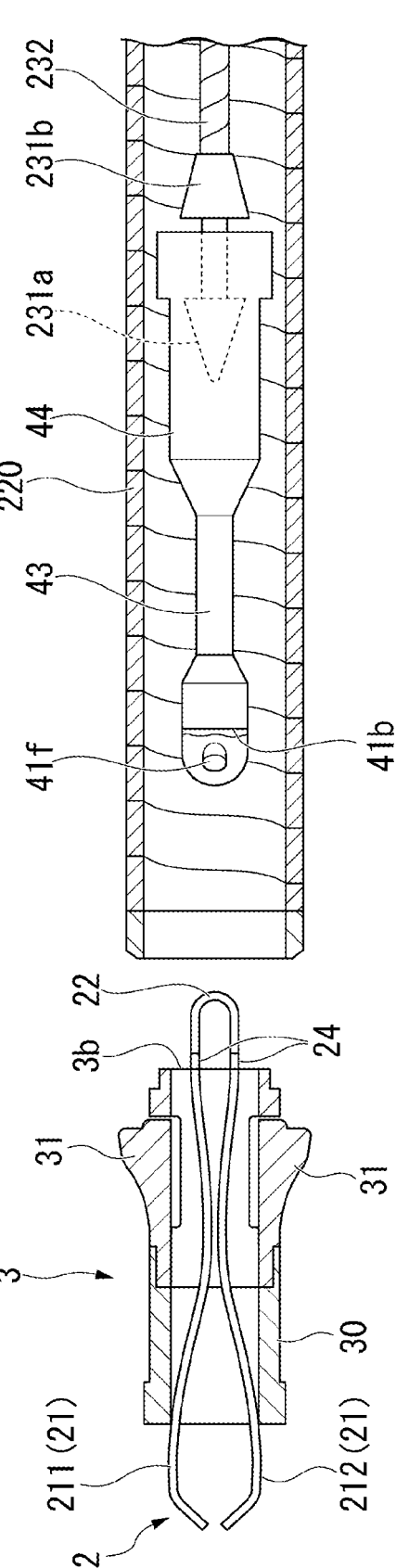
FIG. 26 is a diagram illustrating the clip unit after breakage.

FIG. 26 is a diagram illustrating the clip unit 1 after breaking has occurred.

The user may move the sheath 220 backward and leave the clip 2 having ligated tissue in the body.

With the cartridge system 100 according to this embodiment, when the clip unit 1 is loaded into the clip introduction device 200, almost no gap can be formed between the clip unit 1 and the sheath 220 of the clip introduction device (applicator) 200, and it is possible to more reliably load the clip unit 1 into the clip introduction device 200.

While the first embodiment of the present disclosure has been described above in detail with reference to the drawings, a specific configuration is not limited to this embodiment and includes a change in design without departing from the scope of the present disclosure. Elements described in the aforementioned embodiment and following modified examples can be appropriately combined into a configuration.

Modified Example 1

Figure 27:
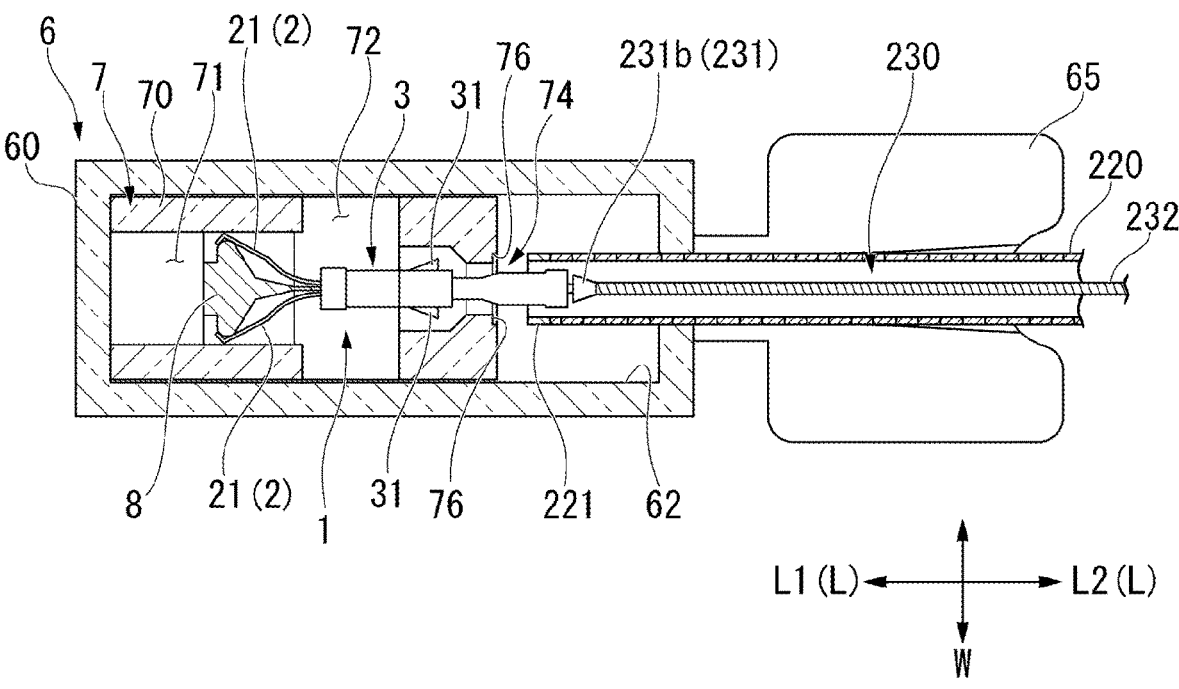
FIG. 27 is a diagram illustrating a modified example of a sheath insertion area.
Figure 28:
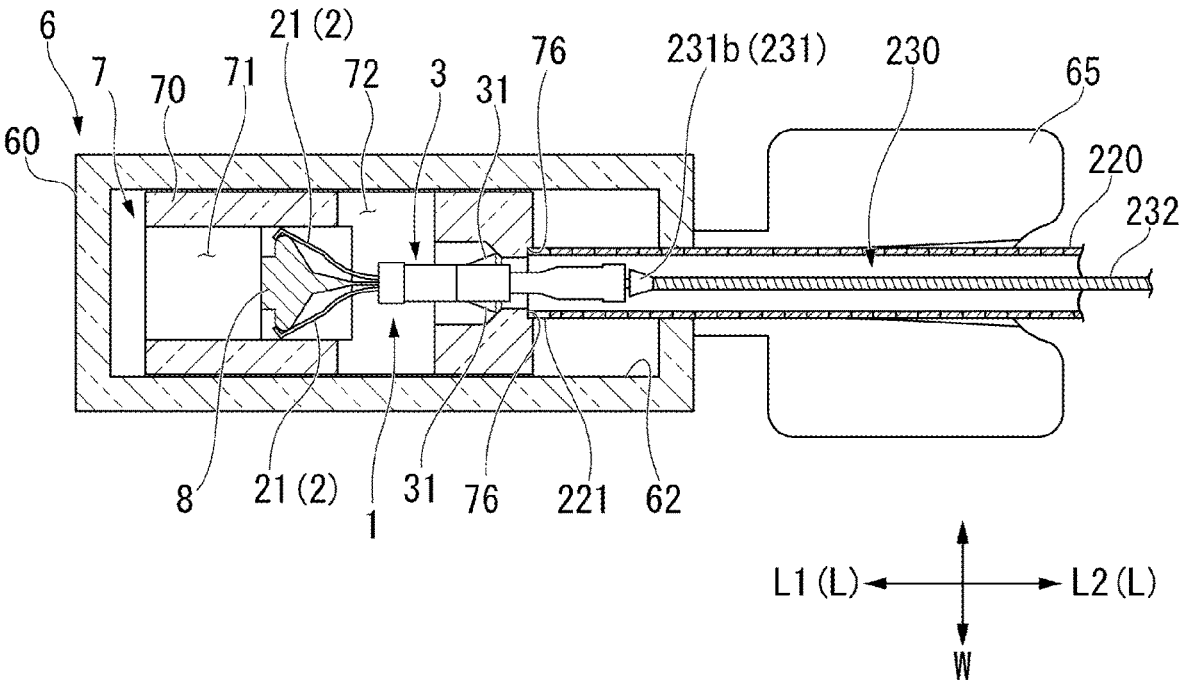
FIG. 28 is a diagram illustrating the modified example.

In the aforementioned embodiment, the length L8 in the length direction L of the sheath insertion area 74 may be smaller than the difference between the length L6 and the length L7 ((L6–L7)>L8). As illustrated in FIGS. 27 and 28, the sheath insertion area 74 may be very short.

Modified Example 2

Figure 29:
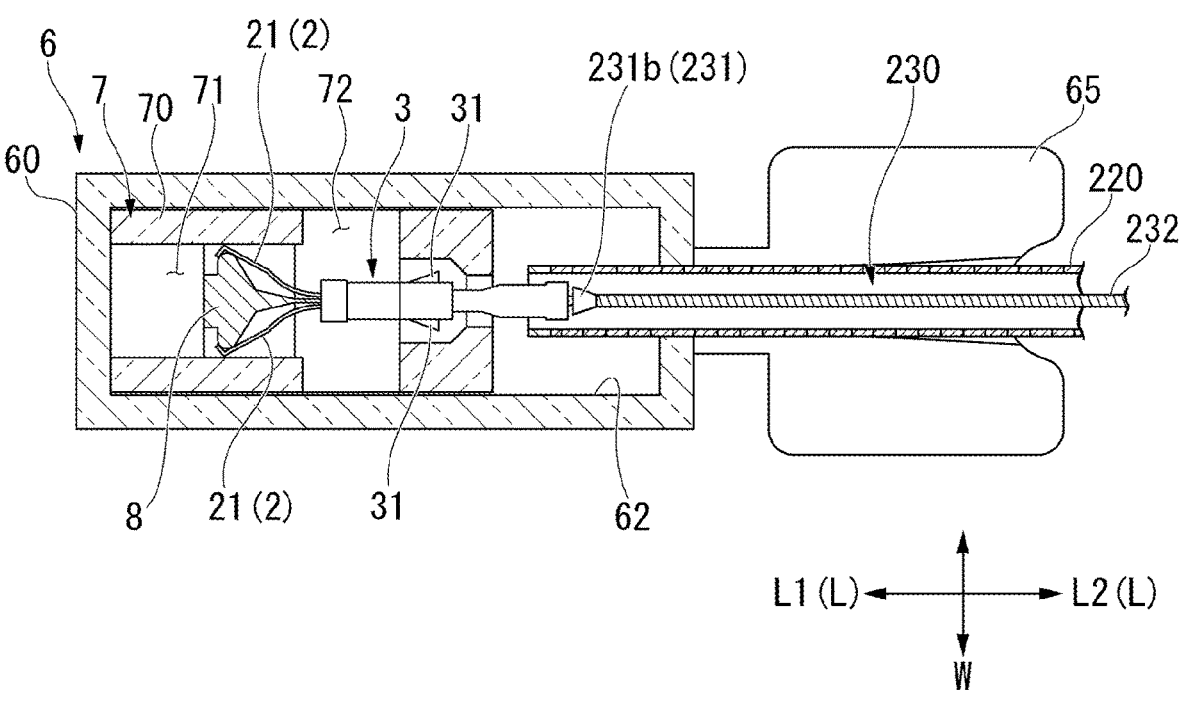
FIG. 29 is a diagram illustrating another modified example of the sheath insertion area.
Figure 30:
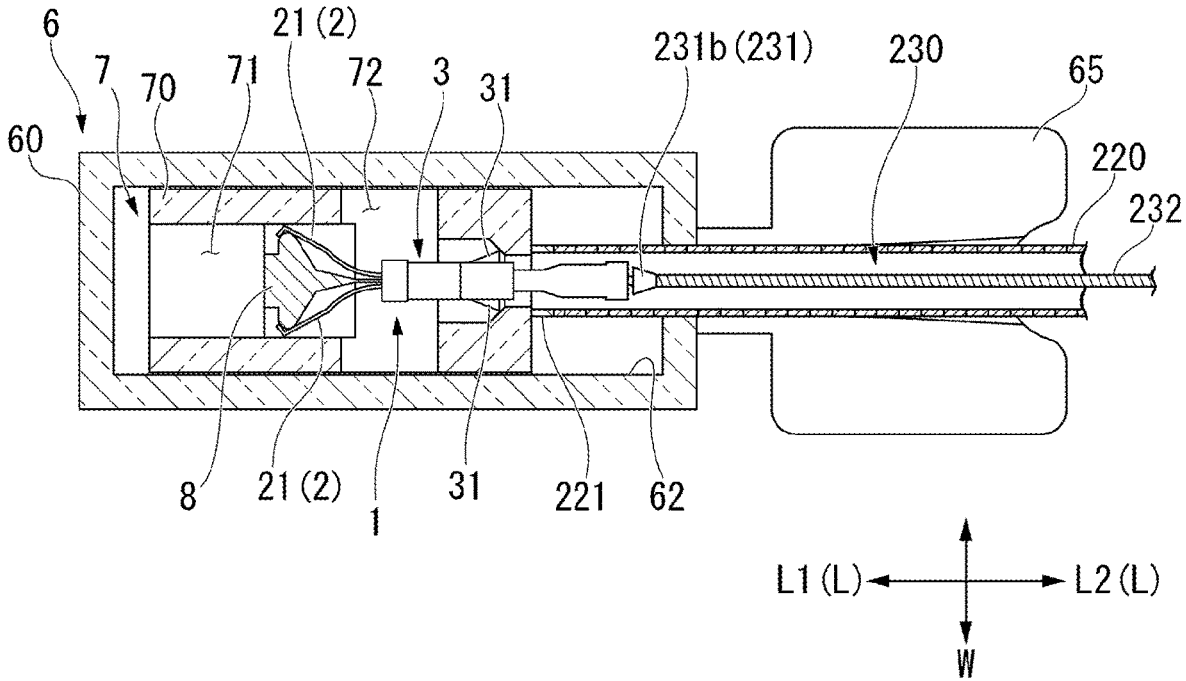
FIG. 30 is a diagram illustrating the modified example.

In the aforementioned embodiment, the length L8 in the length direction L of the sheath insertion area 74 may be smaller than the difference between the length L6 and the length L7 ((L6–L7)>L8). As illustrated in FIGS. 29 and 30, the sheath insertion area 74 may be substantially zero. That is, the sheath insertion area 74 may not be provided.

Second Embodiment

A second embodiment of the present disclosure will be described below with reference to FIGS. 31 to 34. In the following description, the same elements as described above will be referred to by the same reference signs, and repeated description thereof will be omitted.

A cartridge system 100B according to this embodiment may include a clip unit 1B and a cartridge 5B that accommodates, locates, or stores the clip unit 1B. The cartridge system 100B may be a support system that allows the clip unit 1B to be easily loaded into a clip introduction device 200.

Clip Unit 1B

Figure 31:
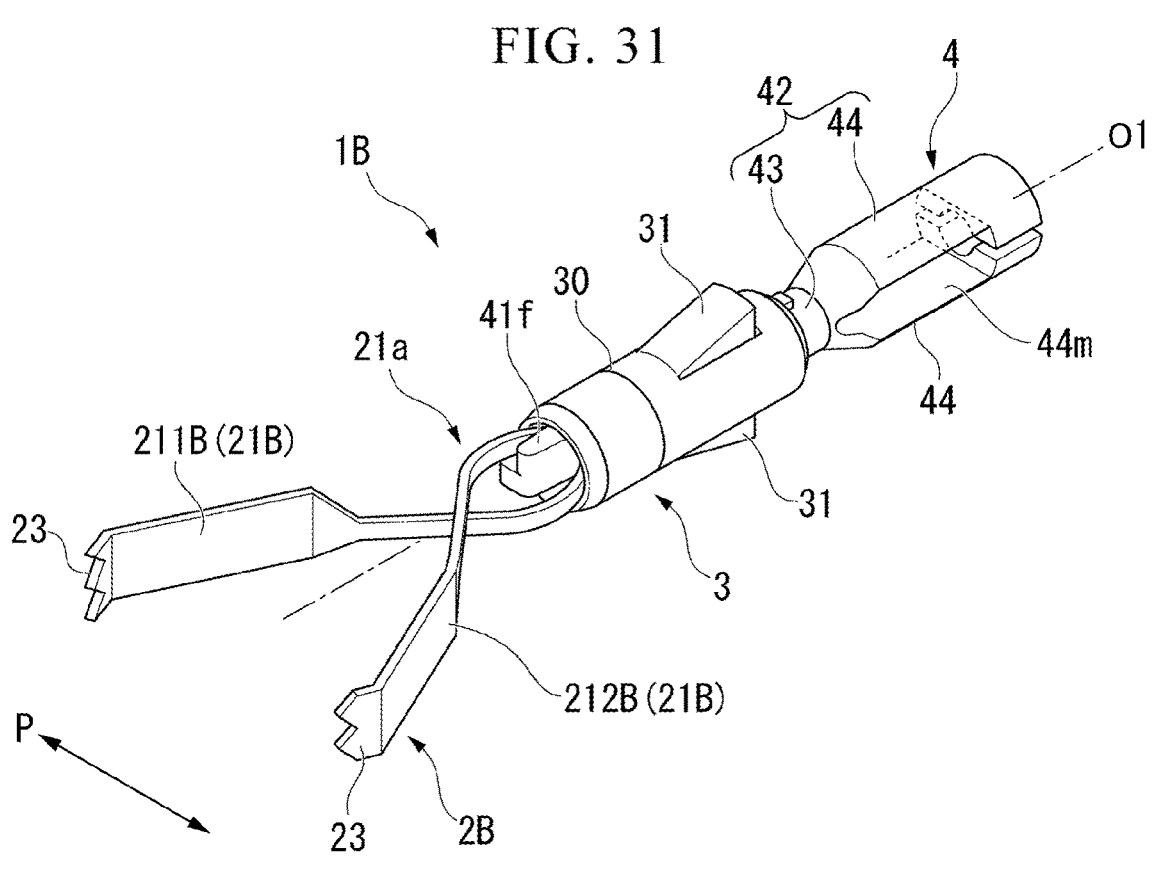
FIG. 31 is a perspective view of a clip unit of a cartridge system according to a second embodiment.

FIG. 31 is a perspective view of the clip unit 1B.

The clip unit 1B may include a clip 2B, a presser tube 3 serving as a fixing member, and a connection member 4.

In the clip 2B, a loop portion 21a may be formed, for example, by bending a metallic plate member such as a leaf spring member formed of a stainless steel material at a central portion thereof. In the clip 2B, a pair of arms 21B having expandability may extend in a state in which the tips thereof move away after crossing the arms at a position close to the loop portion 21a. The pair of arms 21B may include a first arm 211B and a second arm 212B. Tissue grasping portions 23 facing each other may be formed at the tips of the pair of arms 21B.

Cartridge 5B

Figure 32:
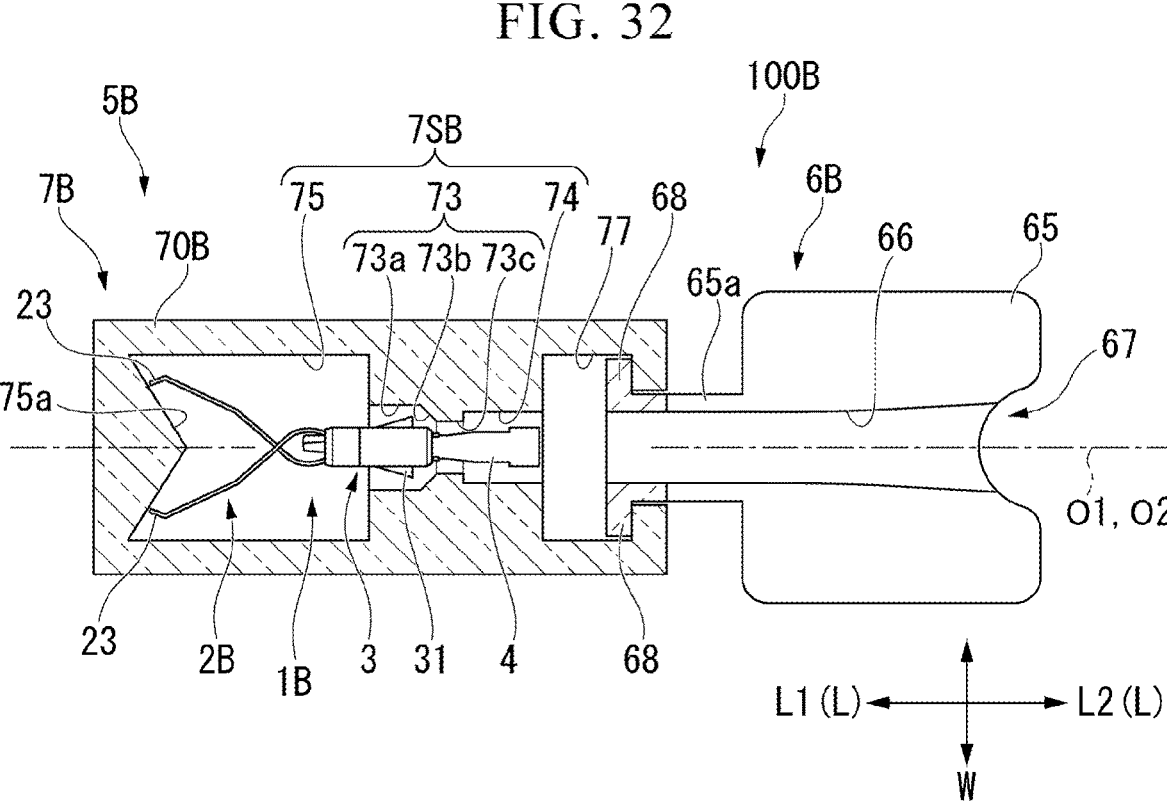
FIG. 32 is a sectional view of a cartridge in which the clip unit is stored.

FIG. 32 is a sectional view of the cartridge 5B in which the clip unit 1B is stored.

The cartridge 5B may include a first cartridge 6B and a second cartridge 7B. The second cartridge 7B may be connected to the first cartridge 6B.

The first cartridge 6B may include a connection portion 68, a compression portion 65, and a sheath connection portion 66. The connection portion 68 may be a member that is provided on the tip side L1 of the sheath connection portion 66 and that is connected to a connected portion 77 of the second cartridge 7B to be movable in the length direction L. In this embodiment, the connection portion 68 may be a protruding portion protruding in the width direction W.

The second cartridge 7B may be formed in a substantially rectangular box shape and may be connected to the connection portion 68 to be movable in the length direction L. The second cartridge 7B may include a cartridge body 70B formed in a substantially rectangular box shape, a storage area 7SB formed in the cartridge body 70B, and a connected portion 77.

The storage area 7SB in which the clip unit 1B may be stored such that the clip unit 1B is movable in the length direction (moving direction) L may be formed in the cartridge body 70B. The storage area 7SB may include an arm accommodation area 75, a folded area 73, and a sheath insertion area 74. The arm accommodation area 75, the folded area 73, and the sheath insertion area 74 may be arranged from the tip side to the base side in the length direction L of the second cartridge 7B. The arm accommodation area 75, the folded area 73, and the sheath insertion area 74 may be internal formed symmetric with respect to the vertical plane VP including the center axis O2 in the length direction L of the storage area 7SB.

The arm accommodation area 75 may be an area in which a pair of arms 21B is accommodated, located, or stored. A tip face 75a formed in a V shape when seen or viewed in the height direction H may be formed on the tip side L1 of the arm accommodation area 75. The tip face 75a may be a face with which the tissue grasping portion 23 of the clip 2B can come into contact.

The connected portion 77 may be a recessed portion provided on the base side L2 of the sheath insertion area 74 and connected to the connection portion 68 of the first cartridge 6B to be movable in the length direction L.

Figure 33:
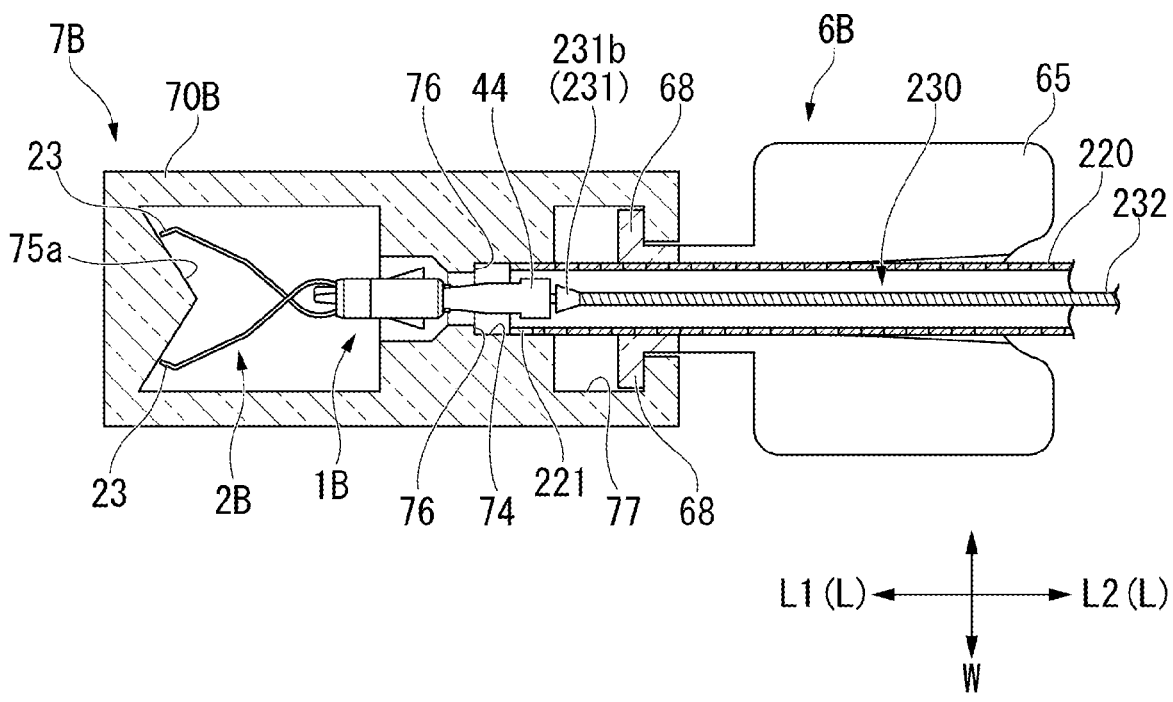
FIG. 33 is a diagram illustrating a method of loading the clip unit into the clip introduction device using the cartridge.
Figure 34:
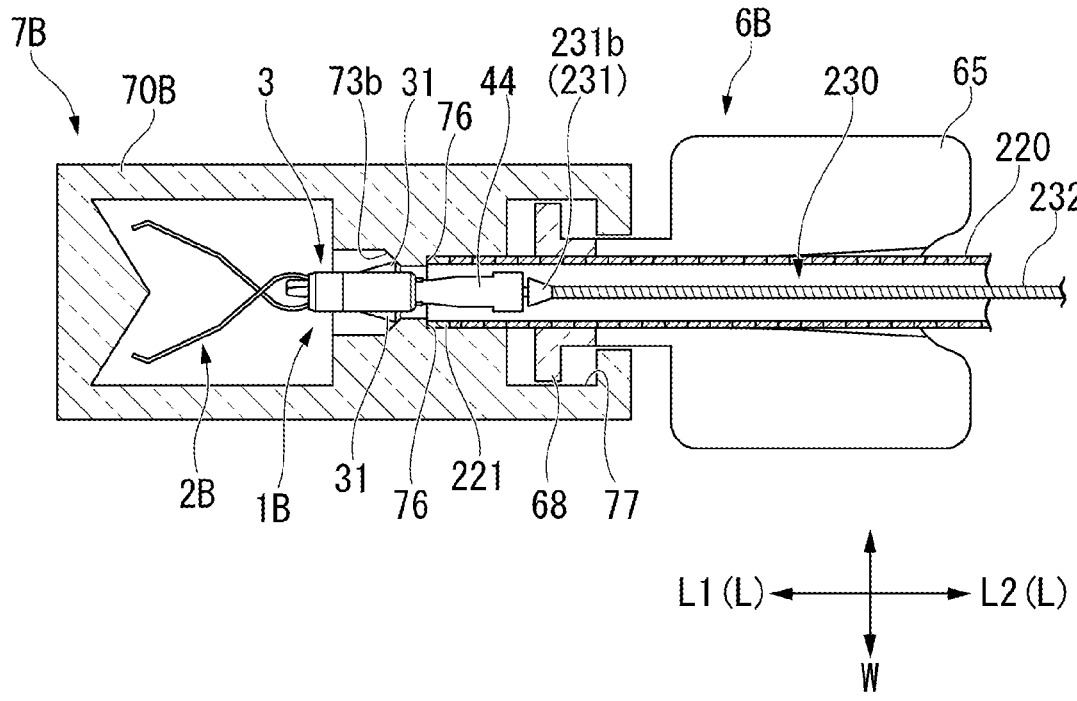
FIG. 34 is a diagram illustrating a method of loading the clip unit into the clip introduction device using the cartridge.

Operations of the cartridge system 100B will be described below. FIGS. 33 and 34 are diagrams illustrating a method of loading the clip unit 1B into the clip introduction device 200 using the cartridge 5B.

A user may insert the sheath 220 into the sheath insertion area 74 via the insertion port 67. In such an example, the distal tip 221 of the sheath 220 illustrated in FIG. 33 does not come into contact with the sheath contact portion 76 of the sheath insertion area 74. The user may fix the sheath 220 to the first cartridge 6B by compressing the sheath 220 with the compression portion 65.

The user may press the connection member 4 with the arrowhead-shaped hook portion 231 by moving the slider 242 forward relative to the operation portion body 241 of the operation portion 240 and moving the operating wire 230 forward relative to the sheath 220 and moves the clip unit 1B forward until the tissue grasping portion 23 comes into contact with the tip face 75a. The user may connect the engagement portion 231a of the arrowhead-shaped hook portion 231 to the elastic arm portion 44 of the connection member 4 by further moving the arrowhead-shaped hook portion 231 forward.

As illustrated in FIG. 34, the user may further pull the clip unit 1B to the base side L2. Since the protruding or retracting wing 31 of the presser tube 3 of the clip unit 1B engages with the tapered portion 73b, the second cartridge 7B along with the clip unit 1B can be pulled to the base side L2. The length L8 in the length direction L of the sheath insertion area 74 may be smaller than the difference between the length L6 and the length L7 ((L6–L7)>L8). Accordingly, the second cartridge 7B can be pulled to the base side L2 until the distal tip 221 of the sheath 220 inserted into the sheath insertion area 74 comes into contact with the sheath contact portion 76.

The user may further pull the clip unit 1B to the base side L2. The presser tube 3 may pass through the folded area 73. When the presser tube 3 slides in the folded area 73 from the tip side L1 to the base side L2, the protruding or retracting wing 31 of the presser tube 3 can become or enter the retracted state in which it can be accommodated, located, or stored in the sheath 220. The protruding or retracting wing 31 can be brought into the retracted state by being pulled into the sheath 220. The protruding or retracting wing 31 pulled into the sheath 220 can be maintained in the retracted state.

The distal tip 221 of the sheath 220 can be in contact with the sheath contact portion 76 and thus almost no gap in the length direction L can be formed between the distal tip 221 and the sheath contact portion 76. Accordingly, the protruding or retracting wing 31 of the presser tube 3 can be smoothly accommodated, located, or stored in the sheath 220.

The user may further pull the operating wire 230. The clip 2B pulled to the base side L2 can be pulled into the internal space of the presser tube 3 and can be pulled into the sheath 220. The clip 2B may be pulled into the sheath 220 without being pulled into the internal space of the presser tube 3. Accordingly, loading of the clip unit 1B into the clip introduction device 200 is completed. The user may decompress the sheath 220 with the compression portion 65 and take out or remove the sheath 220 from the cartridge 5B.

With the cartridge system 100B according to this embodiment, when the clip unit 1B is loaded into the clip introduction device 200, almost no gap is formed between the clip unit 1B and the sheath 220 of the clip introduction device (applicator) 200, and it is possible to more reliably load the clip unit 1B into the clip introduction device 200.

While the second embodiment of the present invention has been described above in details with reference to the drawings, a specific configuration is not limited to this embodiment and includes a change in design without departing from the scope of the present disclosure. Elements described in the aforementioned embodiment and following modified examples can be appropriately combined into a configuration.

Third Embodiment

A third embodiment of the present disclosure will be described below with reference to FIGS. 35 to 39. In the following description, the same elements as described above will be referred to by the same reference signs, and repeated description thereof will be omitted.

Figure 35:
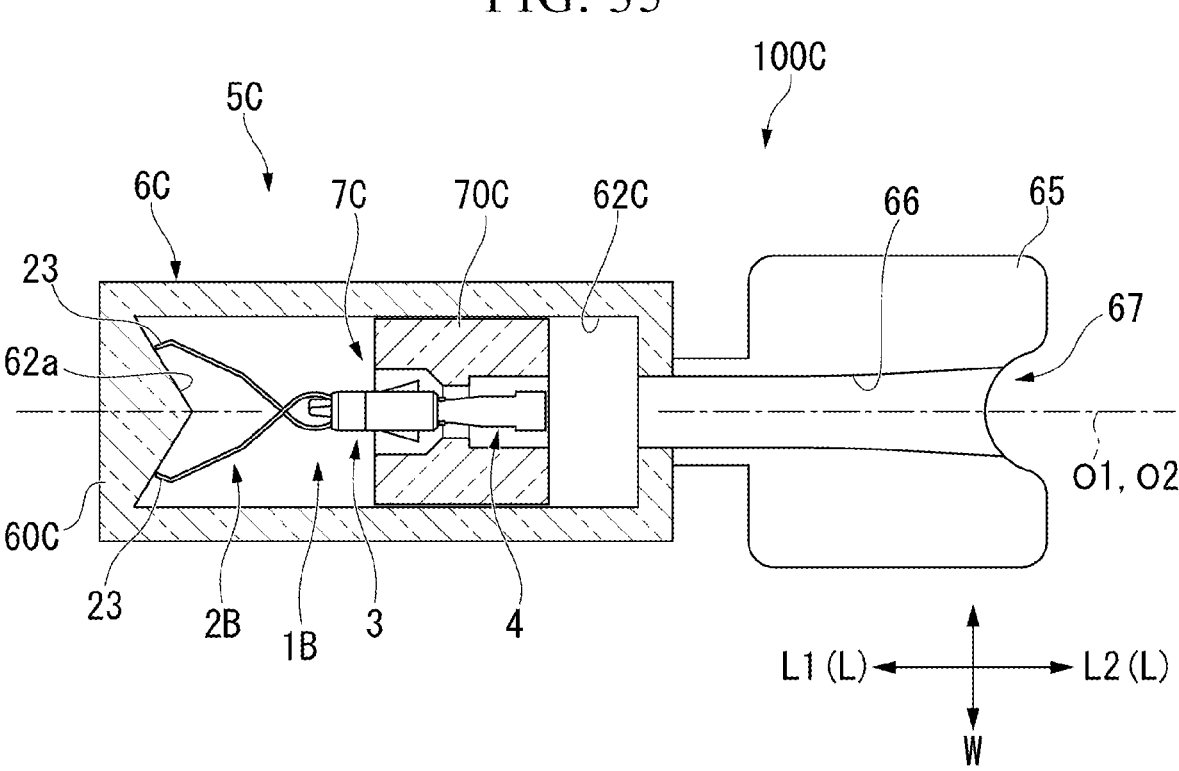
FIG. 35 is a perspective view of a cartridge of a cartridge system according to a third embodiment.

FIG. 35 is a sectional view of a cartridge 5C in which a clip unit 1B is stored.

A cartridge system 100C according to this embodiment may include a clip unit 1B and a cartridge 5C that accommodates, locates, or stores the clip unit 1B. The cartridge system 100C may be a support system that allows the clip unit 1B to be easily loaded into a clip introduction device 200.

Cartridge 5C

The cartridge 5C may include a first cartridge 6C and a second cartridge 7C. The second cartridge 7C may be connected to the first cartridge 6C.

Figure 36:
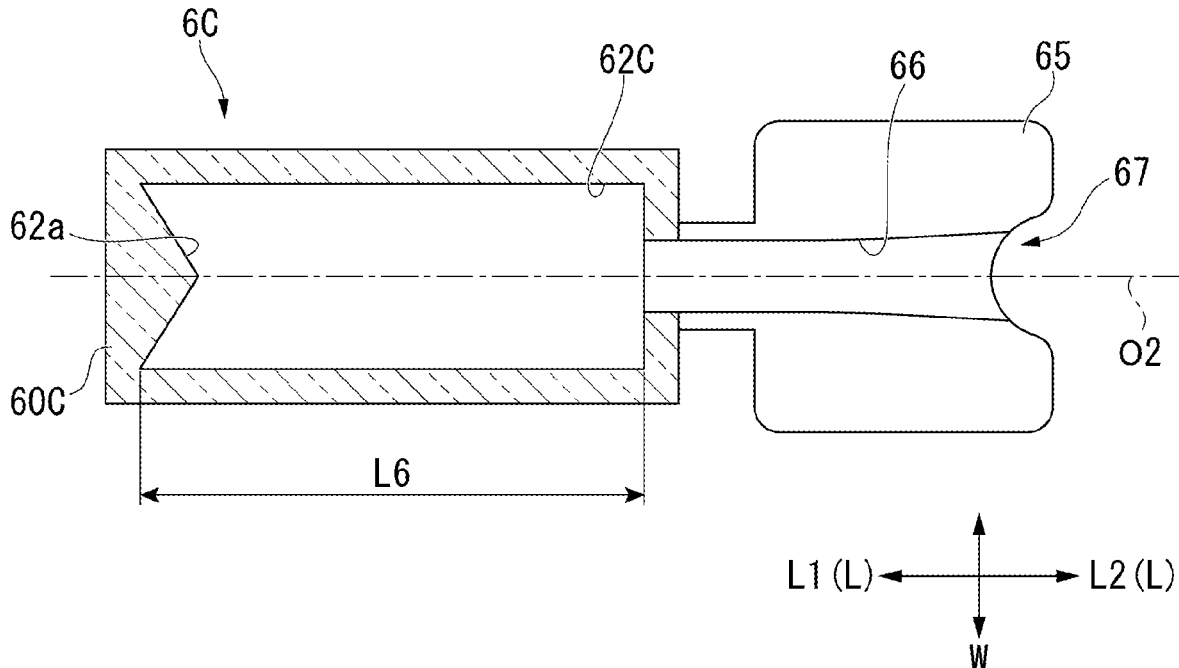
FIG. 36 is a sectional view of a first cartridge of the cartridge.

FIG. 36 is a sectional view of the first cartridge 6C.

The first cartridge 6C may include a cartridge outer circumferential portion 60C, a compression portion 65, and a sheath connection portion 66.

The cartridge outer circumferential portion 60C may be formed in a substantially rectangular box shape. A length in the width direction W of the cartridge outer circumferential portion 60C may be larger than a length in the height direction H of the cartridge outer circumferential portion 60C. The cartridge outer circumferential portion 60C may include a second cartridge accommodation portion 62C.

The second cartridge accommodation portion 62C may be formed in the cartridge outer circumferential portion 60C. The second cartridge accommodation portion 62C may be formed in a substantially rectangular shape when seen or viewed in the height direction H. A tip face 62a formed in a V shape when seen or viewed in the height direction H may be formed on the tip side L1 of the second cartridge accommodation portion 62C. The second cartridge accommodation portion 62C may accommodate , locate, or store the second cartridge 7C to be movable in the length direction L.

Figure 37:
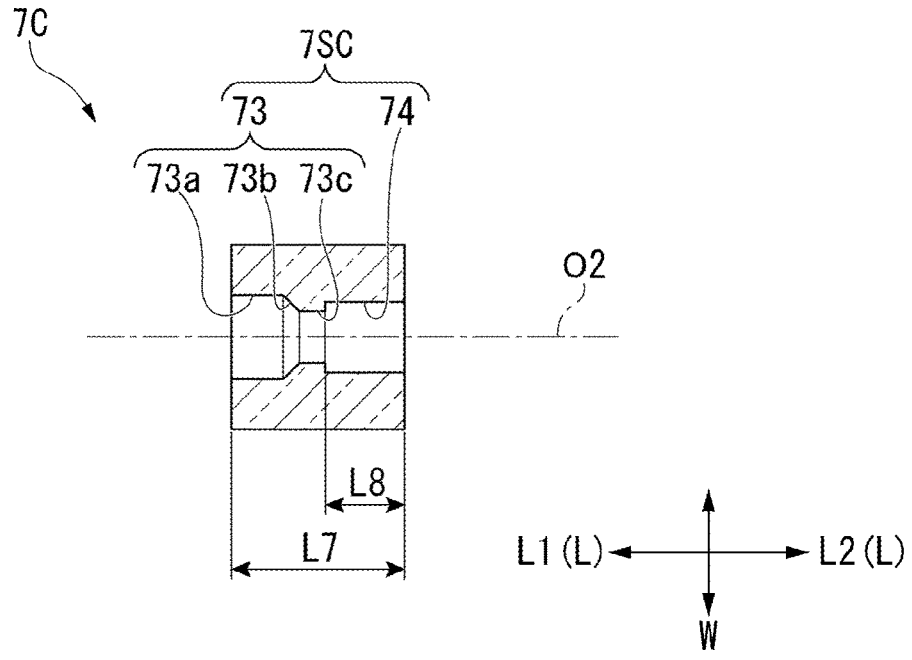
FIG. 37 is a sectional view of a second cartridge of the cartridge.

FIG. 37 is a sectional view of the second cartridge 7C.

The second cartridge 7C may be formed in a substantially rectangular box shape and may be accommodated, located, or stored in the second cartridge accommodation portion 62C to be movable in the length direction L. The length L7 in the length direction L of the second cartridge 7C may be smaller than the length L6 in the length direction L of the second cartridge accommodation portion 62C of the first cartridge 6C. The second cartridge 7C can thus move forward and backward in a length range (L6-L7) in the length direction L.

The second cartridge 7C may include a cartridge body 70C formed in a substantially rectangular box shape and a storage area 7SC formed in the cartridge body 70C.

The storage area 7SC in which the clip unit 1B is stored such that the clip unit 1B is movable in the length direction (moving direction) L may be formed in the cartridge body 70C. The storage area 7SC may include a folded area 73 and a sheath insertion area 74. As illustrated in FIG. 37, the folded area 73 and the sheath insertion area 74 may be arranged from the tip side to the base side in the length direction L of the second cartridge 7C. The folded area 73 and the sheath insertion area 74 may be internal spaces formed symmetric with respect to the vertical plane VP including the center axis O2 in the length direction L of the storage area 7SC.

The second cartridge 7C may be accommodated, located, or stored in the second cartridge accommodation portion 62C such that it is movable along the center axis O2 in the length direction L of the storage area 7SC.

Figure 38:
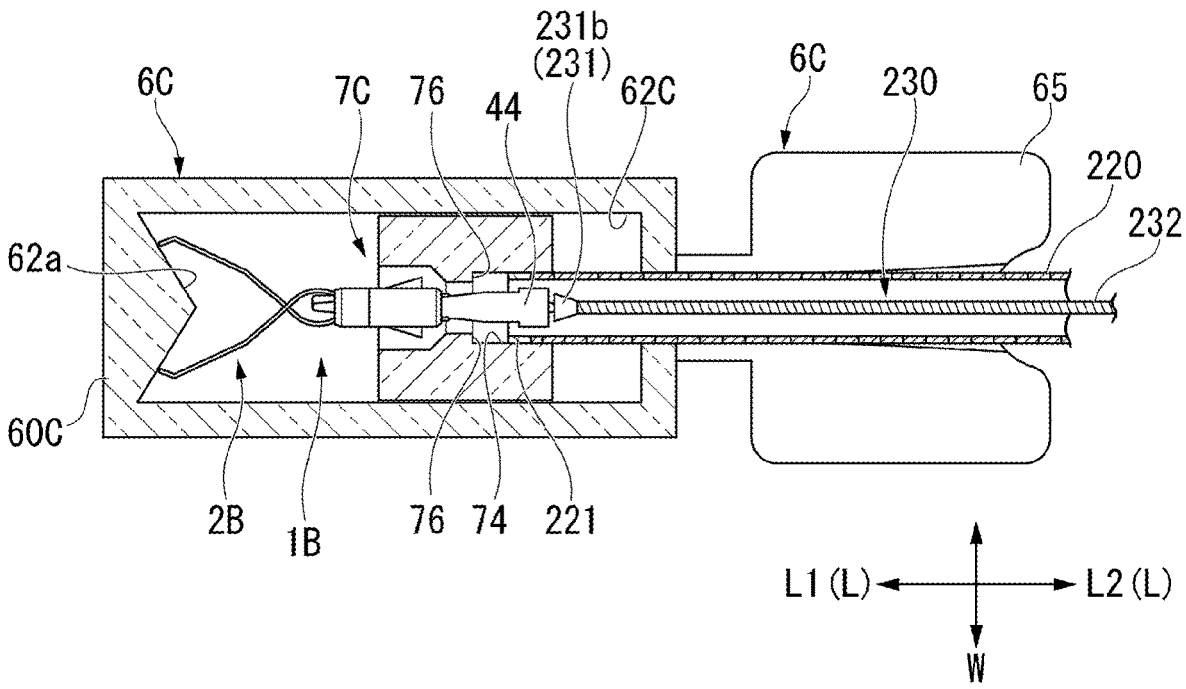
FIG. 38 is a diagram illustrating a method of loading the clip unit of the cartridge system into the clip introduction device using the cartridge.
Figure 39:
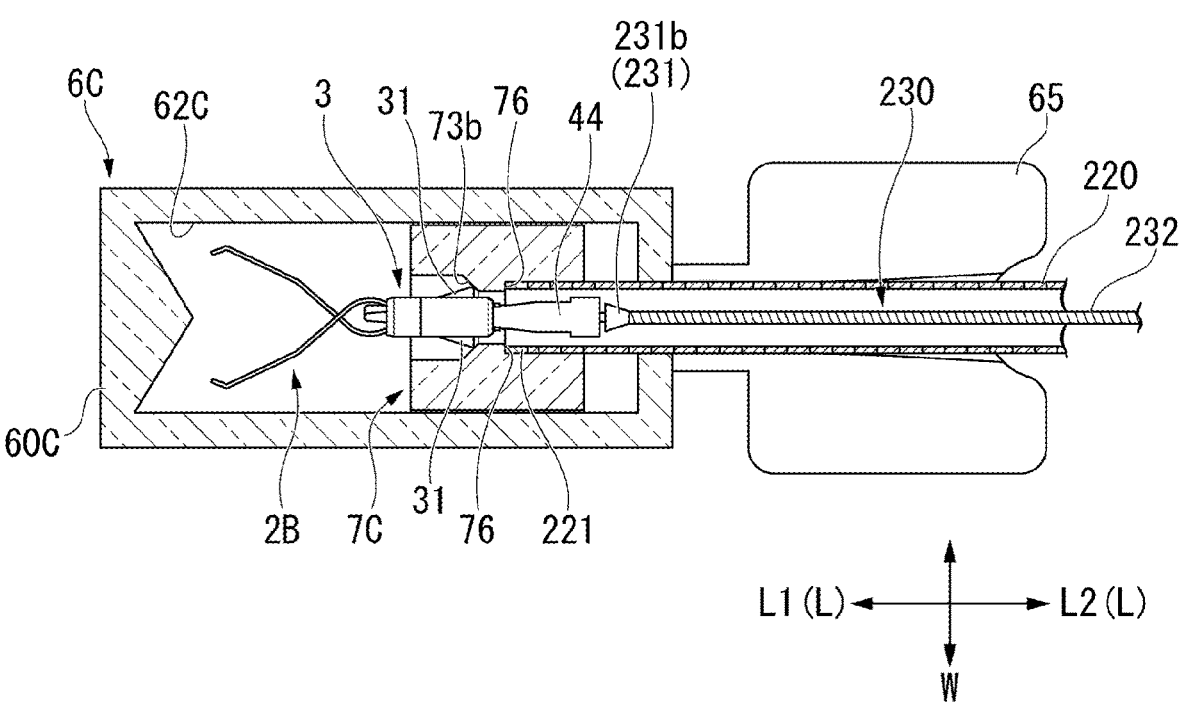
FIG. 39 is a diagram illustrating a method of loading the clip unit of the cartridge system into the clip introduction device using the cartridge.

Operations of the cartridge system 100C will be described below. FIGS. 38 and 39 are diagrams illustrating a method of loading the clip unit 1B into the clip introduction device 200 using the cartridge 5C.

A user may insert the sheath 220 into the sheath insertion area 74 via the insertion port 67. In such an example, distal tip 221 of the sheath 220 illustrated in FIG. 38 does not come into contact with the sheath contact portion 76 of the sheath insertion area 74. The user may fix the sheath 220 to the first cartridge 6C by compressing the sheath 220 with the compression portion 65.

The user may press the connection member 4 with the arrowhead-shaped hook portion 231 by moving the slider 242 forward relative to the operation portion body 241 of the operation portion 240 and moving the operating wire 230 forward relative to the sheath 220 and moves the clip unit 1B forward until the tissue grasping portion 23 comes into contact with the tip face 62a. The user may connect the engagement portion 231a of the arrowhead-shaped hook portion 231 to the elastic arm portion 44 of the connection member 4 by further moving the arrowhead-shaped hook portion 231 forward.

As illustrated in FIG. 39, the user may further pull the clip unit 1B to the base side L2. Since the protruding or retracting wing 31 of the presser tube 3 of the clip unit 1B engages with the tapered portion 73b, the second cartridge 7C along with the clip unit 1B can be pulled to the base side L2. The length L8 in the length direction L of the sheath insertion area 74 may be smaller than the difference between the length L6 and the length L7 ((L6–L7)>L8). Accordingly, the second cartridge 7C may be pulled to the base side L2 until the distal tip 221 of the sheath 220 inserted into the sheath insertion area 74 makes contact with the sheath contact portion 76.

The user may further pull the clip unit 1B to the base side L2. The presser tube 3 may pass through the folded area 73. When the presser tube 3 slides in the folded area 73 from the tip side L1 to the base side L2, the protruding or retracting wing 31 of the presser tube 3 can become or enter the retracted state in which it can be accommodated, located, or stored in the sheath 220. The protruding or retracting wing 31 enters the retracted state by being pulled into the sheath 220. The protruding or retracting wing 31 pulled into the sheath 220 can them maintained in the retracted state.

The distal tip 221 of the sheath 220 may make contact with the sheath contact portion 76 and thus almost no gap in the length direction L can be formed between the distal tip 221 and the sheath contact portion 76. Accordingly, the protruding or retracting wing 31 of the presser tube 3 can be smoothly accommodated, located, or stored in the sheath 220.

The user may further pull the operating wire 230. The clip 2B pulled to the base side L2 may be pulled into the internal space of the presser tube 3 and may be pulled into the sheath 220. The clip 2B may be pulled into the sheath 220 without being pulled into the internal space of the presser tube 3. Accordingly, loading of the clip unit 1B into the clip introduction device 200 is completed. The user may decompress the sheath 220 with the compression portion 65 and remove the sheath 220 from the cartridge 5C.

With the cartridge system 100C according to this embodiment, when the clip unit 1B is loaded into the clip introduction device 200, almost no gap is formed between the clip unit 1B and the sheath 220 of the clip introduction device (applicator) 200, and it is possible to more reliably load the clip unit 1B into the clip introduction device 200.

While the third embodiment of the present invention has been described above in details with reference to the drawings, a specific configuration is not limited to this embodiment and includes a change in design without departing from the scope of the present disclosure. Elements described in the aforementioned embodiment and following modified examples can be appropriately combined into a configuration.

MODIFIED EXAMPLE 3

Figure 40:
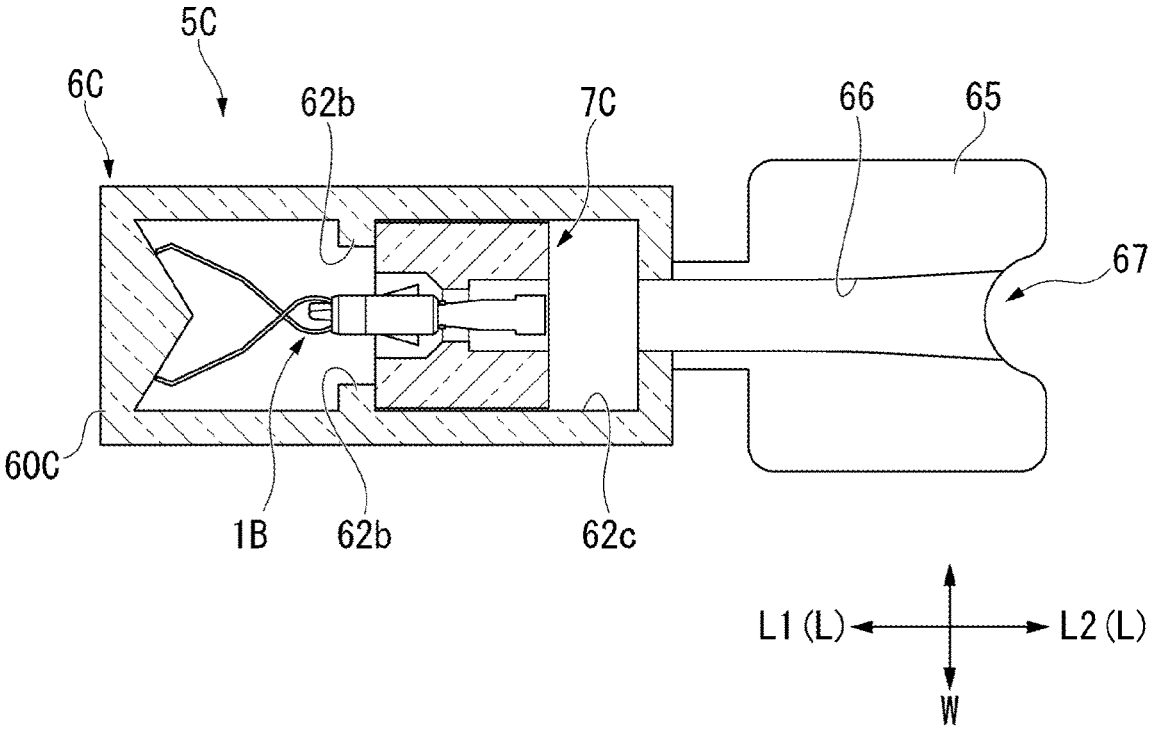
FIG. 40 is a diagram illustrating a modified example of the first cartridge.

FIG. 40 is a diagram illustrating a modified example of the first cartridge 6C. The first cartridge 6C may include a stopper 62b that regulates movement of the second cartridge 7C to the tip side L1 from a predetermined position.

Fourth Embodiment

A fourth embodiment of the present invention will be described below with reference to FIGS. 41 to 48. In the following description, the same elements as described above will be referred to by the same reference signs, and repeated description thereof will be omitted.

Figure 41:
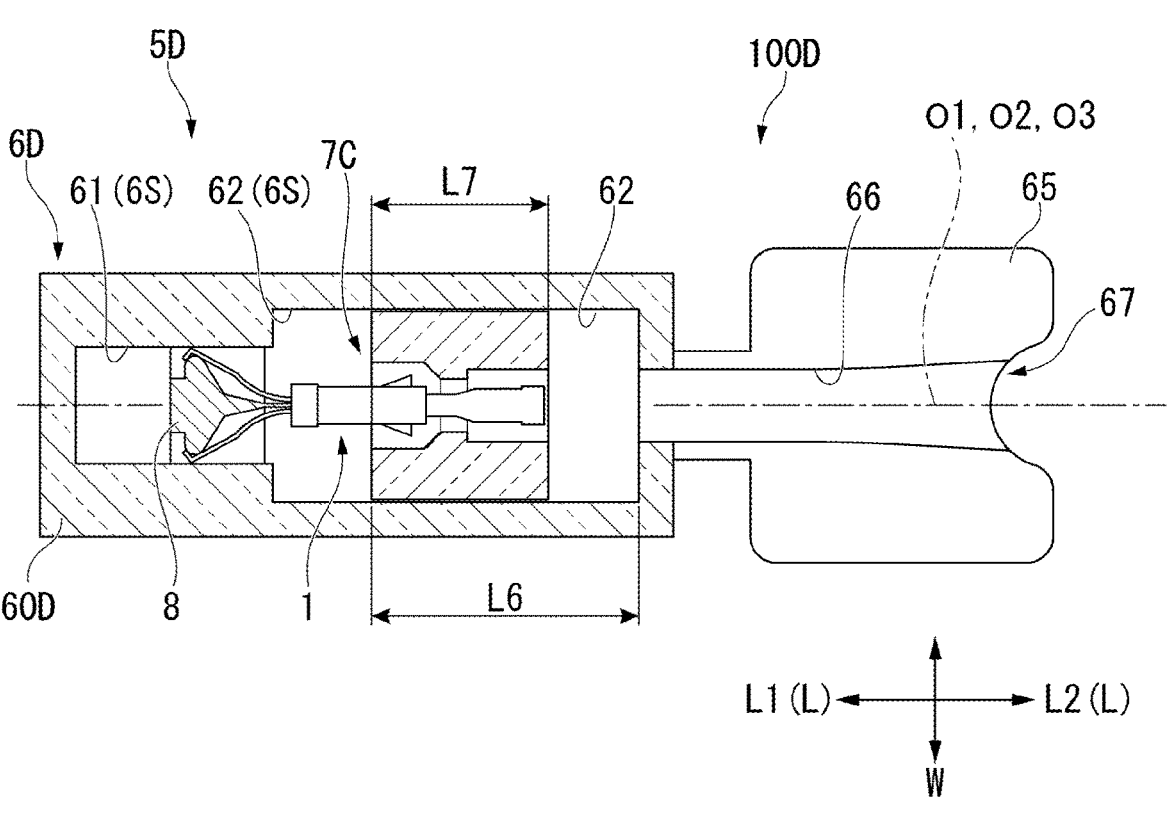
FIG. 41 is a sectional view of a cartridge of a cartridge system according to a fourth embodiment.
Figure 42:
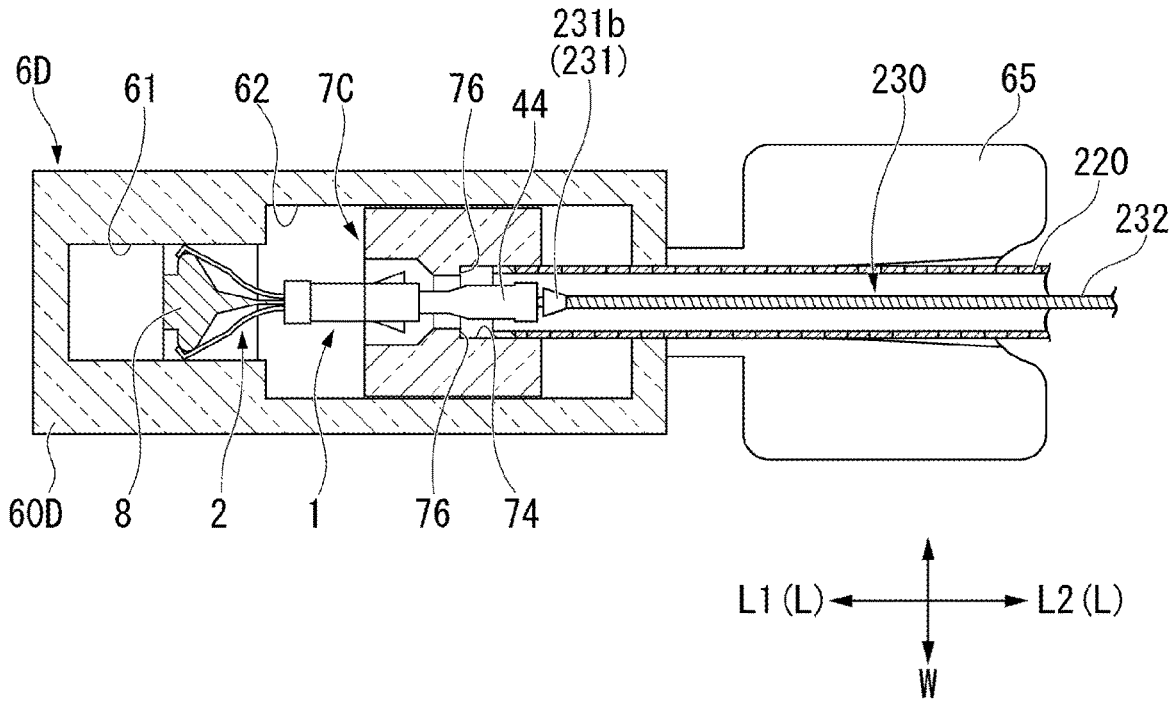
FIG. 42 is a diagram illustrating a method of loading the clip unit of the cartridge system into the clip introduction device using the cartridge.

FIG. 41 is a sectional view of a cartridge 5D in which a clip unit 1 is stored.

A cartridge system 100D according to this embodiment may include a clip unit 1 and a cartridge 5D that may accommodate, locate, or store the clip unit 1. The cartridge system 100D may be a support system that allows the clip unit 1 to be easily loaded into a clip introduction device 200.

Cartridge 5D

The cartridge 5D may include a first cartridge 6D and a second cartridge 7C. The second cartridge 7C may be accommodated, located, or stored in the first cartridge 6D.

The first cartridge 6D may include a cartridge outer circumferential portion 60D, a compression portion 65, and a sheath connection portion 66.

The cartridge outer circumferential portion 60D may be formed in a substantially rectangular box shape. A length in the width direction W of the cartridge outer circumferential portion 60D may be larger than a length in the height direction H of the cartridge outer circumferential portion 60D. A storage area 6S in which the clip unit 1 may be stored to be movable in the length direction (moving direction) L may be formed in the cartridge outer circumferential portion 60D. The storage area 6S may include a first area 61 and a second area 62. The first area 61 and the second area 62 may be formed in the cartridge outer circumferential portion 60D.

The first area 61 may be the same area as the first area 71 according to the first embodiment and may be an internal space in which the clip unit 1 may be stored to be movable in the length direction L. The first area 61 communicates with, contact, connect to, touch, or the like the second area 62.

The second area (second cartridge accommodation portion) 62 may be the same area as the second area 72 according to the first embodiment and may be an internal space in which the clip unit 1 may be stored to be movable in the length direction L. The second area 62 may also serve as the second cartridge accommodation portion 62. The second area (second cartridge accommodation portion) 62 may accommodate, locate, or store the second cartridge 7C to be movable forward and backward in the length direction L.

Operations of the cartridge system 100D will be described below. FIGS. 42 to 48 are diagrams illustrating a method of loading the clip unit 1 into the clip introduction device 200 using the cartridge 5D.

A user may insert the sheath 220 into the sheath insertion area 74 via the insertion port 67. In an example, the distal tip 221 of the sheath 220 illustrated in FIG. 42 does not come into contact with the sheath contact portion 76 of the sheath insertion area 74. The user may fix the sheath 220 to the first cartridge 6D by compressing the sheath 220 with the compression portion 65.

The user may connect the engagement portion 231a of the arrowhead-shaped hook portion 231 to the elastic arm portion 44 of the connection member 4 by moving the slider 242 forward relative to the operation portion body 241 of the operation portion 240 and moving the operating wire 230 forward relative to the sheath 220.

Figure 43:
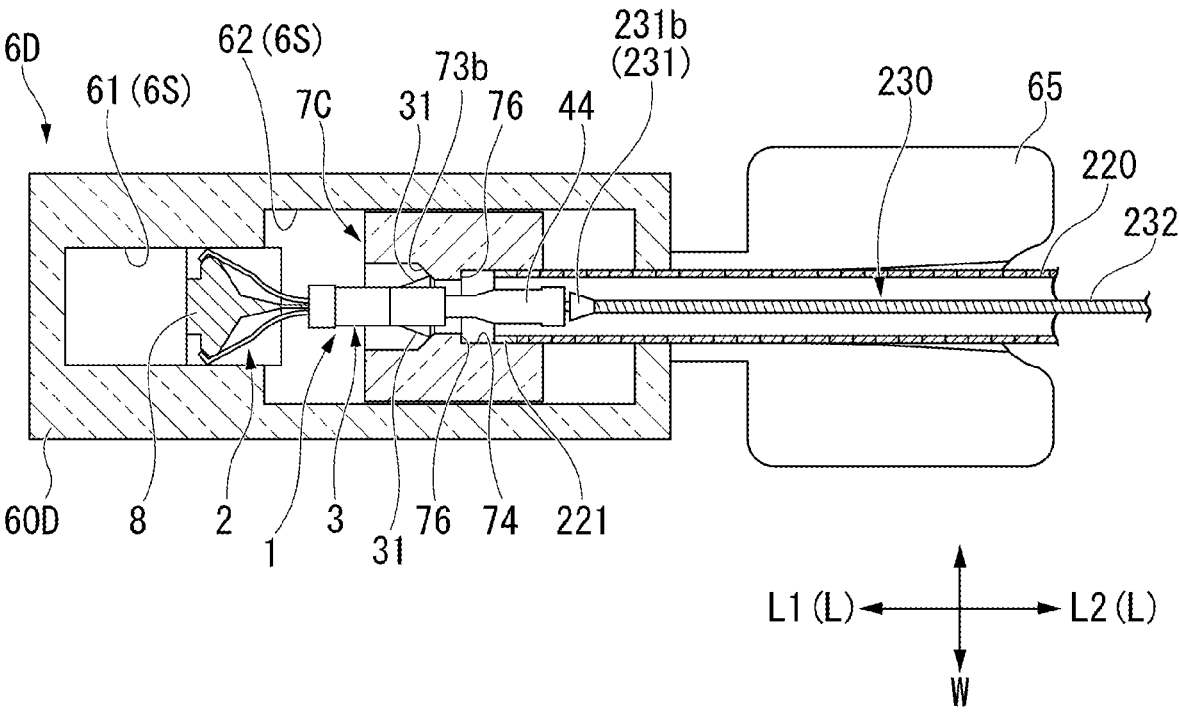
FIG. 43 is a diagram illustrating a method of loading the clip unit of the cartridge system into the clip introduction device using the cartridge.

As illustrated in FIG. 43, the user may pull the operating wire 230. The clip 2 of the clip unit 1 can be pulled to the base side L2 by the connection member 4 connected to the arrowhead-shaped hook portion 231. The hook 41f of the connection member 4 may pull the connection portion 22 of the clip 2 without being broken. The regulation member 8 may move in the first area 61 of the storage area 6S in a state in which it is in contact with the pair of arms 21. Since the pair of arms 21 having a self-expanding force engages with the edge of the tip opening 3a of the presser tube 3, the presser tube 3 along with the clip 2 is also pulled to the base side L2.

The pair of arms 21 may come into contact with the cartridge outer circumferential portion 60D in the opening or closing direction P in the first area 61. It is possible to appropriately prevent the clip 2 from being pulled into the internal space of the presser tube 3 and being locked in the closed state by the presser tube 3 due to a frictional force generated by contact between the pair of arms 21 and the cartridge outer circumferential portion 60D.

When the clip 2 is pulled to the base side L2, the pushing portion 84 of the regulation member 8 can engage with the edge of the tip opening 3a of the presser tube 3. Thus, the minimum approach distance between the clip 2 and the presser tube 3 can be regulated. The pushing portion 84 may make contact with the presser tube 3 in a state in which it is in contact with the pair of arms 21 by pulling the operating wire 230 and regulates movement of the regulation member 8 relative to the presser tube 3. Accordingly, it is also possible to appropriately prevent the clip 2 pulled to the base side L2 by the connection member 4 from being pulled into the internal space of the presser tube 3 and being locked in the closed state by the presser tube 3.

Figure 44:
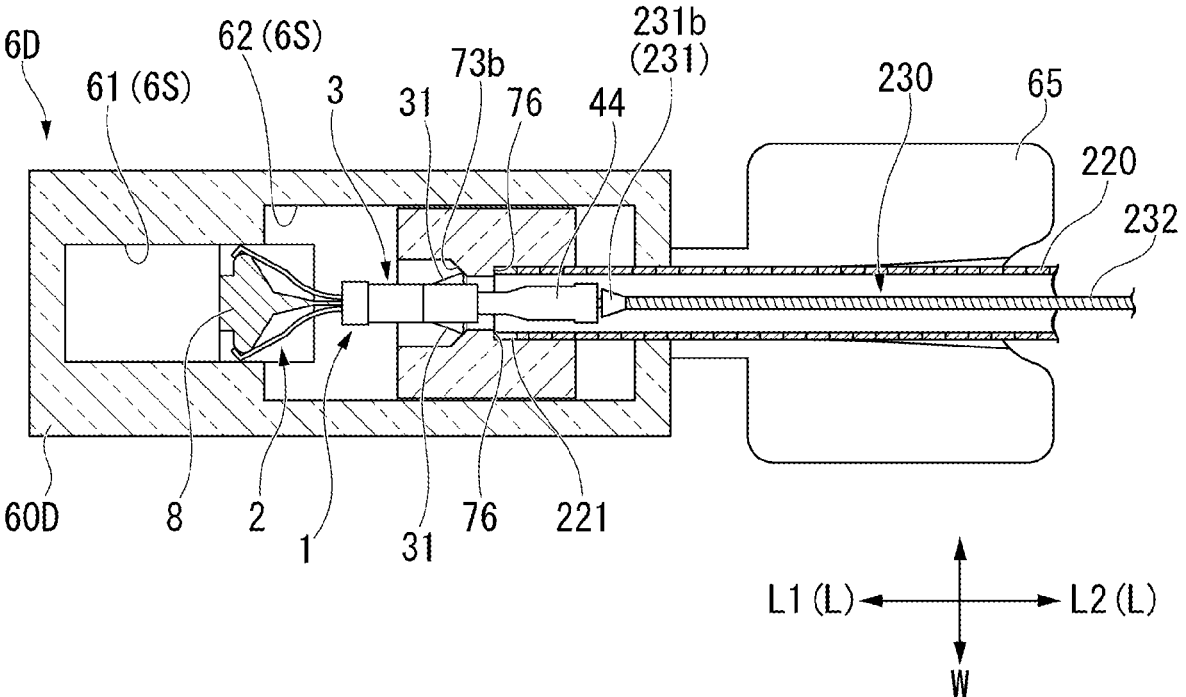
FIG. 44 is a diagram illustrating a method of loading the clip unit of the cartridge system into the clip introduction device using the cartridge.

As illustrated in FIG. 44, the user may further pull the clip unit 1 to the base side L2. Since the protruding or retracting wing 31 of the presser tube 3 of the clip unit 1 engages with the tapered portion 73*b*, the second cartridge 7C along with the clip unit 1 can be pulled to the base side L2. As described above, the length L8 in the length direction L of the sheath insertion area 74 may be smaller than the difference between the length L6 and the length L7 ((L6−L7)>L8). Accordingly, the second cartridge 7C can be pulled to the base side L2 until the distal tip 221 of the sheath 220 inserted into the sheath insertion area 74 comes into contact with the sheath contact portion 76.

Figure 45:
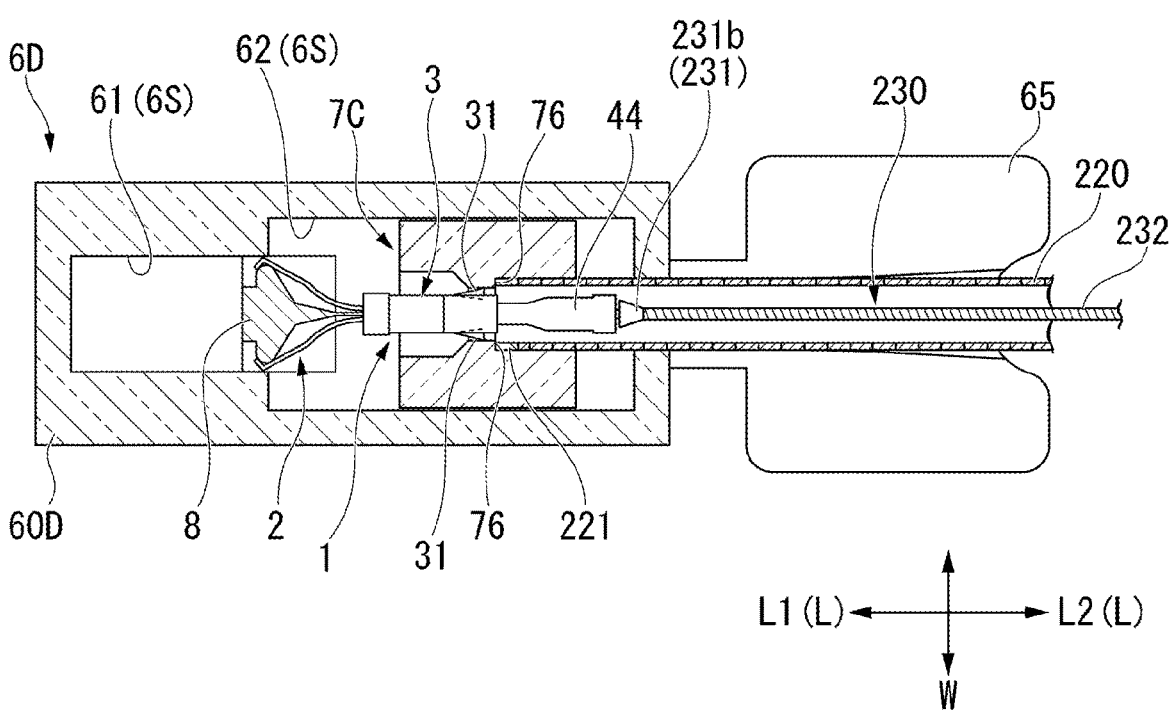
FIG. 45 is a diagram illustrating a method of loading the clip unit of the cartridge system into the clip introduction device using the cartridge.

The user may further pull the clip unit 1 to the base side L2. The presser tube 3 may pass through the folded area 73 as illustrated in FIG. 45. When the presser tube 3 slides in the folded area 73 from the tip side L1 to the base side L2, the protruding or retracting wing 31 of the presser tube 3 may enter the retracted state in which it can be accommodated, located, or stored in the sheath 220. The protruding or retracting wing 31 cab be brought into the retracted state by being pulled into the sheath 220. The protruding or retracting wing 31 pulled into the sheath 220 can then be maintained in the retracted state.

The distal tip 221 of the sheath 220 may make contact with the sheath contact portion 76 and thus almost no gap in the length direction L can be formed between the distal tip 221 and the sheath contact portion 76. Accordingly, the protruding or retracting wing 31 of the presser tube 3 can be smoothly accommodated, located, or stored in the sheath 220.

Figure 46:
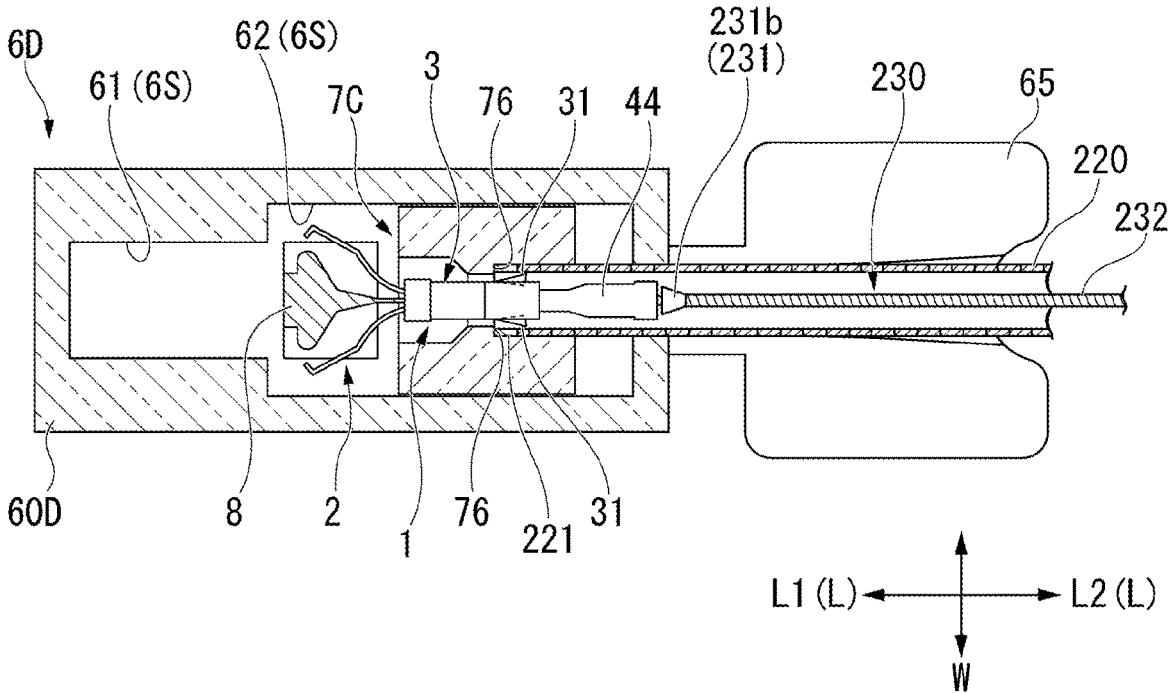
FIG. 46 is a diagram illustrating a method of loading the clip unit of the cartridge system into the clip introduction device using the cartridge.

As illustrated in FIG. 46, the user may further pull the operating wire 230 and pull the regulation member 8 to the second area 62. The length W2 in the width direction W of the second area 62 may be larger than the opening width W3 of the pair of arms 21 in the open state. Accordingly, the regulation member 8 is not grasped by the pair of arms 21 in the second area 62.

Figure 47:
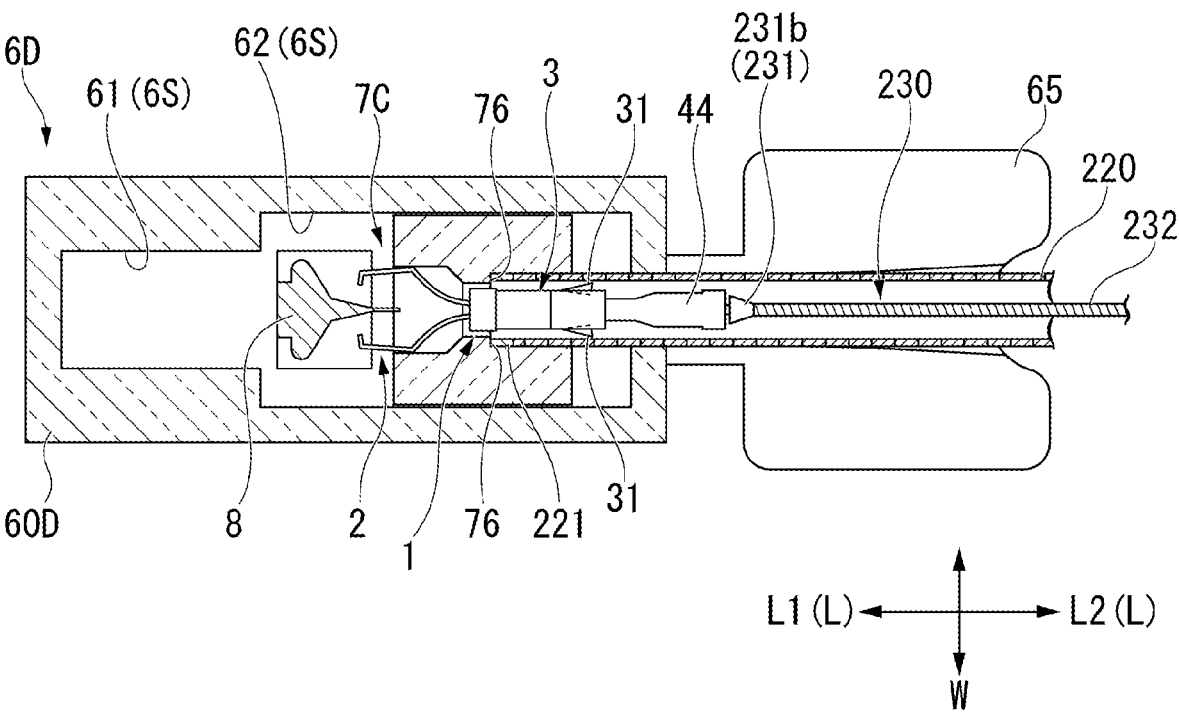
FIG. 47 is a diagram illustrating a method of loading the clip unit of the cartridge system into the clip introduction device using the cartridge.

As illustrated in FIG. 47, the user may further pull the operating wire 230. The clip 2 may be detached from the regulation member 8 and pulled to the base side L2. In the regulation member 8, the tapered portion 83 may be formed on the base side L2 of the protruding portion 82 grasped by the pair of arms 21. Accordingly, when the regulation member 8 is pulled to the base side L2, it is difficult to hook the pair of arms 21 to the regulation member 8.

Figure 48:
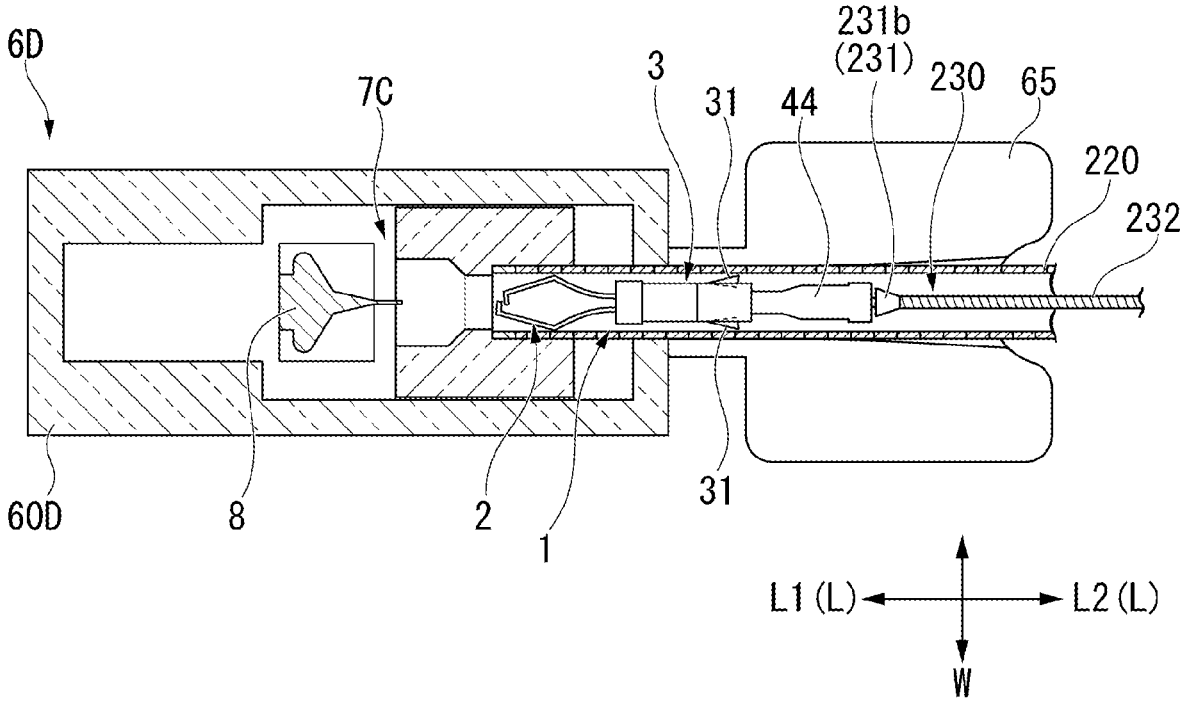
FIG. 48 is a diagram illustrating a method of loading the clip unit of the cartridge system into the clip introduction device using the cartridge.

As illustrated in FIG. 48, the user may further pull the operating wire 230. Since the pair of arms 21 does not grasp the regulation member 8, the minimum approach distance between the clip 2 and the presser tube 3 is not regulated. The clip 2 pulled to the base side L2 is pulled into the internal space of the presser tube 3 and may be pulled into the sheath 220. The clip 2 may be pulled into the sheath 220 without being pulled into the internal space of the presser tube 3. Accordingly, loading of the clip unit 1 into the clip introduction device 200 is completed. The user may decompress the sheath 220 with the compression portion 65 and remove the sheath 220 from the cartridge 5D.

With the cartridge system 100D according to this embodiment, when the clip unit 1 is loaded into the clip introduction device 200, almost no gap can be formed between the clip unit 1 and the sheath 220 of the clip introduction device (applicator) 200, and it is possible to more reliably load the clip unit 1 into the clip introduction device 200.

While the fourth embodiment of the present invention has been described above in details with reference to the drawings, a specific configuration is not limited to this embodiment and includes a change in design without departing from the scope of the present disclosure. Elements described in the aforementioned embodiment and following modified examples can be appropriately combined into a configuration.

MODIFIED EXAMPLE 4

Figure 49:
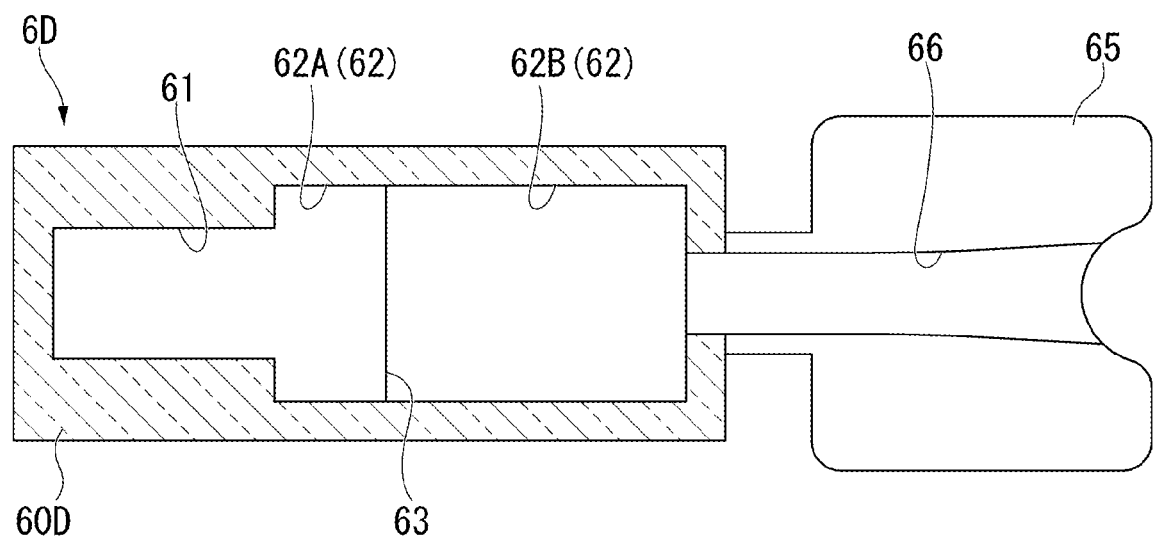
FIG. 49 is a diagram illustrating a modified example of a second area of a first cartridge of the cartridge.

FIG. 49 is a diagram illustrating a modified example of the second area 62. As illustrated in FIG. 49, the second area 62 may include a stepped portion 63 for clearly partitioning a second area 62A and a second cartridge accommodation portion 62B.

EXPLANATION OF REFERENCES 100, 100B, 100C, 100D . . . Cartridge system
200 . . . Clip introduction device (applicator)
300 . . . Clip device
1, 1B . . . Clip unit
2, 2B . . . Clip
3 . . . Presser tube
4 . . . Connection member
5, 5B, 5C, 5D . . . Cartridge
6, 6B, 6C, 6D . . . First cartridge
6S . . . Storage area
60, 60C, 60D . . . Cartridge outer circumferential portion
61 . . . First area
62, 62A, 62B, 62C . . . Second area (second cartridge accommodation portion)
62*a* . . . Tip face
62*b* . . . Stopper
63 . . . Stepped portion
65 . . . Compression portion (plate)
651 . . . First compression portion
652 . . . Second compression portion
65*a* . . . Connection portion
65*b* . . . Gap
66 . . . Sheath connection portion
66*a* . . . Straight portion
66*b* . . . Tapered portion
67 . . . Insertion port
68 . . . Connection portion
7, 7B, 7C . . . Second cartridge
7S, 7SB, 7SC . . . Storage area
70, 70B, 70C . . . Cartridge body
71 . . . First area
72 . . . Second area
73 . . . Folded area
73*a* . . . Diameter-increased portion
73*b* . . . Tapered portion
73*c* . . . Diameter-decreased portion
74 . . . Sheath insertion area
75 . . . Arm accommodation area
75*a* . . . Tip face
76 . . . Sheath contact portion
77 . . . Connected portion
8 . . . Regulation member
80 . . . Auxiliary member
81 . . . Tip
82 . . . Protruding portion
82*b* . . . Maximum protruding point
82*c* . . . Contact point
83 . . . Tapered portion

83*b* . . . Tapered portion
84 . . . Pushing portion

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

What is claimed is:

1. A cartridge comprising:
a first cartridge including an insertion port configured to receive a sheath of an applicator; and
a second cartridge including a storage area configured to store at least a part of a clip unit, wherein the second cartridge is configured to be stored in the first cartridge and is movable relative to the first cartridge in a moving direction of the clip unit.

2. The cartridge according to claim 1, wherein the first cartridge includes a plate configured to fix the sheath inserted into the insertion port relative to the first cartridge, and wherein the storage area includes a sheath insertion area into which a tip of the sheath inserted into the insertion port is inserted.

3. The cartridge according to claim 2, wherein the first cartridge includes a connection portion provided on a tip side of the insertion port, wherein the second cartridge includes a connected portion provided on a base side of the sheath insertion area, and wherein the connection portion and the connected portion are connected to be movable in the moving direction.

4. The cartridge according to claim 2, wherein the storage area includes a folded area configured to retract wings of the clip unit, and wherein the second cartridge is configured to be pulled until the second cartridge comes into contact with the tip of the sheath inserted into the sheath insertion area.

5. The cartridge according to claim 4, wherein the second cartridge comes into contact with the tip of the sheath as the clip unit is pulled relative to the sheath to engage with the folded area.

6. The cartridge according to claim 4, wherein the folded area makes contact with the sheath insertion area, and wherein in a width direction perpendicular to the moving direction of the clip unit, a length of a part in which the folded area and the sheath insertion area are connected is larger than a length of the folded area.

7. The cartridge according to claim 6, wherein a contact face is configured to come into contact with a tip of the sheath, the contact face is provided on a side of the sheath insertion area including the folded area.

8. The cartridge according to claim 1, wherein the second cartridge is connected to the first cartridge.

9. The cartridge according to claim 4, further comprising:
a regulation member configured to be grasped by the clip, wherein the storage area of the second cartridge further includes a first area and a second area, wherein the first area, the second area, the folded area, and the sheath insertion area are arranged in the moving direction, wherein the clip unit is configured to be stored in the storage area in a state in which the clip grasps the regulation member in the first area, wherein a length in a width direction of the first area is smaller than an opening width of the clip in an open state, the width direction of the first area is perpendicular to the moving direction of the sheath insertion area, and wherein a length in a width direction of the second area is larger than the opening width of the clip in the open state, the width direction of the second area is perpendicular to the moving direction of the sheath insertion area.

10. The cartridge according to claim 1, further comprising:
a regulation member configured to be grasped by the clip, wherein the first cartridge includes a storage area in which the clip unit is movably stored, wherein the storage area of the first cartridge includes a first area and a second area, wherein the clip unit is configured to be stored in the storage area of the first cartridge in a state in which the clip grasps the regulation member in the first area, wherein a length in a width direction of the first area is smaller than an opening width of the clip in an open state, the width direction of the first area is perpendicular to the moving direction of the sheath insertion area, wherein a length in a width direction of the second area is larger than the opening width of the clip in the open state, the width direction of the first area is perpendicular to the moving direction of the sheath insertion area, and wherein the second cartridge is movably stored in the second area.

11. The cartridge according to claim 1, wherein the moving direction is a longitudinal direction of the first cartridge, and wherein the second cartridge is configured to store the clip unit in a state in which a distal end of the clip unit protrudes from the second cartridge.

12. A cartridge system comprising:
a clip unit including a clip;
a pipe including wings configured to protrude and retract;
a connector including a connection arm configured to be connected to an applicator;
a first cartridge including an insertion port configured to insert a sheath of the applicator; and
a second cartridge, wherein the second cartridge includes a storage area configured to store at least a part of the clip unit in a state in which the clip unit is movable, wherein the second cartridge is configured to be stored in the first cartridge and is movable relative to the first cartridge in a moving direction of the clip unit.

13. The cartridge system according to claim 12, wherein the first cartridge includes a plate configured to fix the sheath inserted into the insertion port relative to the first cartridge, and wherein the storage area includes a sheath insertion area into which a tip of the sheath inserted into the insertion port is inserted.

14. The cartridge system according to claim 13, wherein the storage area includes a folded area in which the wings of the clip unit are changed to a retracted state when the clip unit is pulled in the moving direction, the retracted state being a state in which the wings are stored in the sheath, and wherein the second cartridge is configured to be pulled until the second cartridge comes into contact with the tip of the sheath inserted into the sheath insertion area, and wherein the second cartridge comes into contact with the tip of the sheath as the clip unit are pulled relative to the sheath to engage with the folded area.

15. The cartridge system according to claim 14, wherein the folded area makes contact with the sheath insertion area, and wherein a width direction perpendicular to the moving direction of the sheath insertion area, a length in the width direction in a part in which the folded area and the sheath insertion area are connected is larger than a length in the width direction of the folded area.

16. The cartridge system according to claim 15, wherein a contact face configured to come into contact with the tip of the sheath, the contact face is provided on a side of the sheath insertion area including the folded area.

17. The cartridge system according to claim 12, wherein the second cartridge is connected to the first cartridge.

18. The cartridge system according to claim 12, wherein the moving direction is a longitudinal direction of the first cartridge, and wherein the second cartridge is configured to store the clip unit in a state in which a distal end of the clip unit protrudes from the second cartridge.

19. A clip cartridge comprising:
a clip including:
a clip arm;
a connector connected to clip arm;
a pipe into which the connector is inserted, the pipe including a pipe body, a wing protruding from the pipe body; and
a cartridge including:
a first cartridge having a storage area, the storage into which the clip is stored; and
a second cartridge located in the storage area, the second cartridge is configured to move relative to the first cartridge in a longitudinal direction of the clip, the second cartridge include a through hole, wherein the through hole has a first diameter and the second diameter, wherein the first diameter is larger than the second diameter, and wherein the second diameter is smaller than a diameter of the wing.

20. The clip cartridge according to claim 19, wherein the cartridge further includes a protrusion, the protrusion is located in the storage area, the protrusion is located proximal relative to the second cartridge, the protrusion is sandwiched between the clip arm, the protrusion configured to move relative to the first cartridge in the longitudinal direction of the clip.

* * * * *